(12) United States Patent
Ricotta et al.

(10) Patent No.: US 11,870,920 B2
(45) Date of Patent: Jan. 9, 2024

(54) GRAPH MODELS OF RELATIONSHIPS BETWEEN DATA STORED IN BLOCKS ON DISTRIBUTED LEDGERS THAT ARE LEARNED THROUGH MACHINE LEARNING AND PLATFORMS FOR CREATING, CATALOGING, AND STORING THE SAME

(71) Applicant: BurstIQ, Inc., Denver, CO (US)

(72) Inventors: Frank J. Ricotta, Colorado Springs, CO (US); Brian Jackson, Parker, CO (US); Tyson Henry, Monument, CO (US); Amber Hartley, Lakewood, CO (US)

(73) Assignee: BurstIQ, Inc., Denver, CO (US)

( * ) Notice: Subject to any disclaimer, the term of this patent is extended or adjusted under 35 U.S.C. 154(b) by 0 days.

(21) Appl. No.: 17/951,760

(22) Filed: Sep. 23, 2022

(65) Prior Publication Data
US 2023/0092365 A1 Mar. 23, 2023

Related U.S. Application Data

(60) Provisional application No. 63/247,718, filed on Sep. 23, 2021.

(51) Int. Cl.
| G06F 7/00 | (2006.01) |
| G06F 16/00 | (2019.01) |
| H04L 9/00 | (2022.01) |
| G06F 16/901 | (2019.01) |
| H04L 9/32 | (2006.01) |
| G06F 16/23 | (2019.01) |
| G06F 16/27 | (2019.01) |
| G16H 50/70 | (2018.01) |

(52) U.S. Cl.
CPC ............ *H04L 9/50* (2022.05); *G06F 16/2379* (2019.01); *G06F 16/27* (2019.01); *G06F 16/9024* (2019.01); *G16H 50/70* (2018.01); *H04L 9/3236* (2013.01)

(58) Field of Classification Search
USPC .................................................. 707/705–767
See application file for complete search history.

(56) References Cited

U.S. PATENT DOCUMENTS

| 2019/0012466 A1 | 1/2019 | Ricotta et al. |
| 2020/0389309 A1* | 12/2020 | Ricotta ................. H04L 9/3239 |
| 2021/0073285 A1* | 3/2021 | Hunter ...................... G06F 8/65 |
| 2021/0117408 A1* | 4/2021 | Figueredo De Santana ................ G06F 16/9027 |
| 2022/0058282 A1 | 2/2022 | Ricotta et al. |

* cited by examiner

*Primary Examiner* — Tuan A Pham
(74) *Attorney, Agent, or Firm* — Perkins Coie LLP

(57) ABSTRACT

Introduced here is a computational architecture (also referred to as a "computational infrastructure") that addresses the limitations of traditional data management solutions using a highly secure data management solution coupled with consent-based sharing. At a high level, the computational architecture applies blockchain methodologies to both transaction data and business data such that both types of data are stored "on chain" in the same computational architecture. This enables several significant advantages over traditional data management solutions with respect to data security, data ownership, data sharing, and intelligence.

11 Claims, 24 Drawing Sheets

610

```
consents 4bed39ae399bd1 ...
for chain_name
when asset.identifier = 15131
until date('2019-12-12T12:43:22-0000')
only attr3, attr4, attr5
```

```
consents 4bed39ae399bd1 ... , 825763ff373aca...
for chain_name
when asset.identifier = 15131
until date('2019-12-12T12:43:22-0000')
only attr3, attr4, attr5
```

```
consents 'researcher'
for chain_name
when asset.identifier = 15131
until date('2019-12-12T12:43:22-0000')
only attr3, attr4, attr5
```

```
consents 4bed39ae399bd1
for chain_name
when asset.test_type = 'CBC'
until date('2019-12-12T12:43:22-0000')
only attr3, attr4, attr5
```

```
consents 'researcher'
for chain_name
when asset.test_type = 'CBC' and asset.location_id = '42'
until date('2019-12-12T12:43:22-0000')
only attr3, attr4, attr5
```

FIGURE 6E

Training Stage
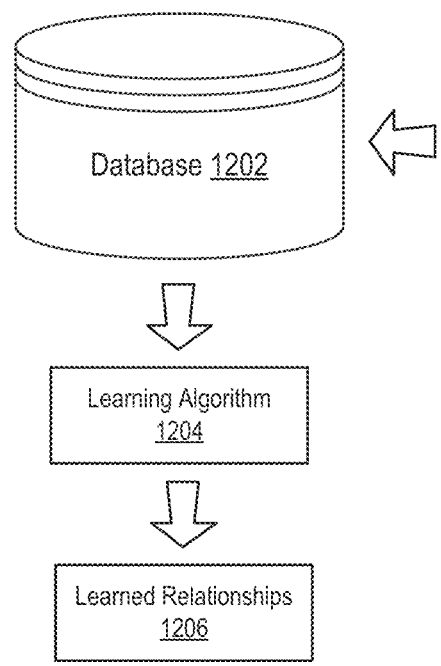
Data Pertaining To Health-Related Entities Including:
- Patients
- Providers
- Payers
- Manufacturers of Medical Equipment
- Pharmaceutical Companies
Inferencing Stage
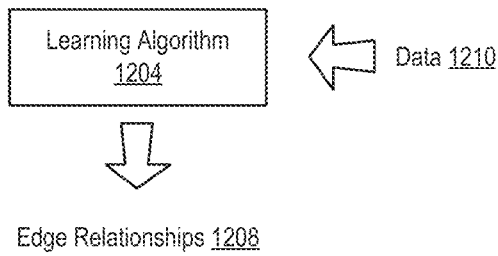
FIGURE 12

1400

1401
Provide (i) a plurality of nodes that collectively implement a blockchain and (ii) a plurality of graph databases that are distributed amongst the plurality of nodes 1402
Generate a hash value upon receiving input indicative of a request to store first data in the corresponding graph database 1403
Upon confirming that the hash value has also been generated by a majority of the plurality of nodes, create a first block that includes (i) the first data and (ii) the hash value 1404
Determine that a contextual relationship exists between the first data in the first block and second data in a second block that is part of the blockchain 1405
Populate information regarding the contextual relationship in the first block 1406
Add the first block onto the blockchain for distribution to the plurality of nodes and storage in the plurality of graph databases 1407
Model the contextual relationship by representing the first and second blocks as graph nodes in a graph data structure and interconnecting the graph nodes with an edge to indicate the relationship

Provide (i) a plurality of nodes that collectively implement a blockchain and (ii) a plurality of graph databases that are distributed amongst the plurality of nodes

1502

Generate a hash value upon receiving input indicative of a request to store first data in the corresponding graph database

1503

Upon confirming that the hash value has also been generated by a majority of the plurality of nodes, configure a first block to have an appropriate field count, an appropriate field size, and/or an appropriate field schema to accommodate the first data

1504

Populate the first data in the first block

1505

Determine that a contextual relationship exists between the first data in the first block and second data in a second block that is part of the blockchain

1506

Populate information regarding the contextual relationship in the first block

1507

Add the first block onto the blockchain for distribution to the plurality of nodes and storage in the plurality of graph databases

GRAPH MODELS OF RELATIONSHIPS BETWEEN DATA STORED IN BLOCKS ON DISTRIBUTED LEDGERS THAT ARE LEARNED THROUGH MACHINE LEARNING AND PLATFORMS FOR CREATING, CATALOGING, AND STORING THE SAME

CROSS-REFERENCE TO RELATED APPLICATIONS

This application claims priority to U.S. Provisional Application No. 63/247,718, titled "Graph Models Of Relationships Between Information Stored On Distributed Ledgers That Are Learned Through Machine Learning," and filed on Sep. 23, 2021, which is incorporated by reference herein in its entirety.

TECHNICAL FIELD

Various embodiments concern approaches to learning the relationships between information stored on a computational architecture, producing visual representations of those relationships, and applying those relationships to an artificial intelligence computation.

BACKGROUND

The term "blockchain" generally refers to a growing list of digital records—referred to as "blocks" that are linked together using cryptography. Generally, each block is representative of a data structure that includes a cryptographic hash of the previous block, a timestamp, and transaction data (or simply "data"). The timestamp proves that the data existed when the block was published in order to get into its cryptographic hash. Since each block includes information about the preceding block, these blocks form a chain, with each new block reinforcing the ones before it. This approach makes blockchains resistant to modification because once recorded, the data in any given block are essentially immutable unless all subsequent blocks are altered.

Blockchains are normally managed by a peer-to-peer network for use as a distributed ledger, where network nodes collectively adhere to a consensus protocol (or simply "protocol") to communicate and then validate new blocks. Blocks are not unalterable—for example, forks can occur where a blockchain splits into two paths—but blockchains are considered a form of distributed computational architecture that is secure by design.

Generally speaking, there are two main types of blockchains, public blockchains and private blockchains. The term "public blockchain" is used to refer to a blockchain that has no access restrictions, and thus is readily accessible to anyone via the Internet. Anyone may be able to send transactions to a public blockchain, as well as become a validator (i.e., participate in the execution of the corresponding protocol). The term "private blockchain," meanwhile, is used to refer to a blockchain that is permissioned. Simply put, one may not be able to join a private blockchain unless invited by a network administrator (or simply "administrator"). Participant and validator access to private blockchains is typically restricted.

In conventional blockchains, data is stored in non-optimized or indexed flat files. Searching for a block or piece of data in a flat file storage medium is linear. In order to perform generalized queries such as those required for analytics, machine learning (ML), and artificial intelligence (AI), a blockchain typically requires a two-step data gathering and validating effort before computations can be performed. This carries several notable drawbacks. First, this two-step process significantly increases the operational overhead and time required to perform the computations. Second, the information being analyzed loses the benefits of immutability, auditability, and cryptographic security that are conferred by implementation on the blockchain.

Additionally, most conventional blockchains contain a fixed block structure and a fixed set of data fields (or simply "fields") that define what data can be stored on the block. Said another way, most conventional blockchains have a fixed count and structure of fields. This further restricts usefulness in performing analytics, ML, and AI, since different types of data would need to be stored on different blockchains. Moreover, the two-step process described above would need to be performed for each blockchain—multiplying the operational overhead described above.

Users of conventional blockchains, especially enterprise users, would prefer that computationally relevant data be unified and that immutability, auditability, and ownership be preserved throughout the computational process, since that provides a richer data experience and prevents the operational hassle and security issues associated with having data stored in multiple places. However, due to the operational hassle and security issues associated with storing data on conventional blockchains, many implementations forego the immutability, auditability, and ownership benefits of blockchains, instead storing the computationally relevant information in "off-chain" data storage with only a hash value (or simply "hash") being stored "on chain."

BRIEF DESCRIPTION OF THE DRAWINGS

FIGS. 6A-E include examples that show how a consent contract can grant access to data in data blocks.

FIG. 12 includes a high-level illustration of a process by which an algorithm can be learned for predicting, inferring, or otherwise determining relationships between dissimilar data.

FIG. 14 includes a flow diagram of a process performed by a computational architecture for committing a block to a blockchain, for storage in a plurality of graph databases that are distributed amongst a plurality of nodes.

FIG. 15 includes a flow diagram of a process performed by a computational architecture for committing a dynamically configurable block to a blockchain, for storage in a plurality of graph databases that are distributed amongst a plurality of nodes.

Figure 1:
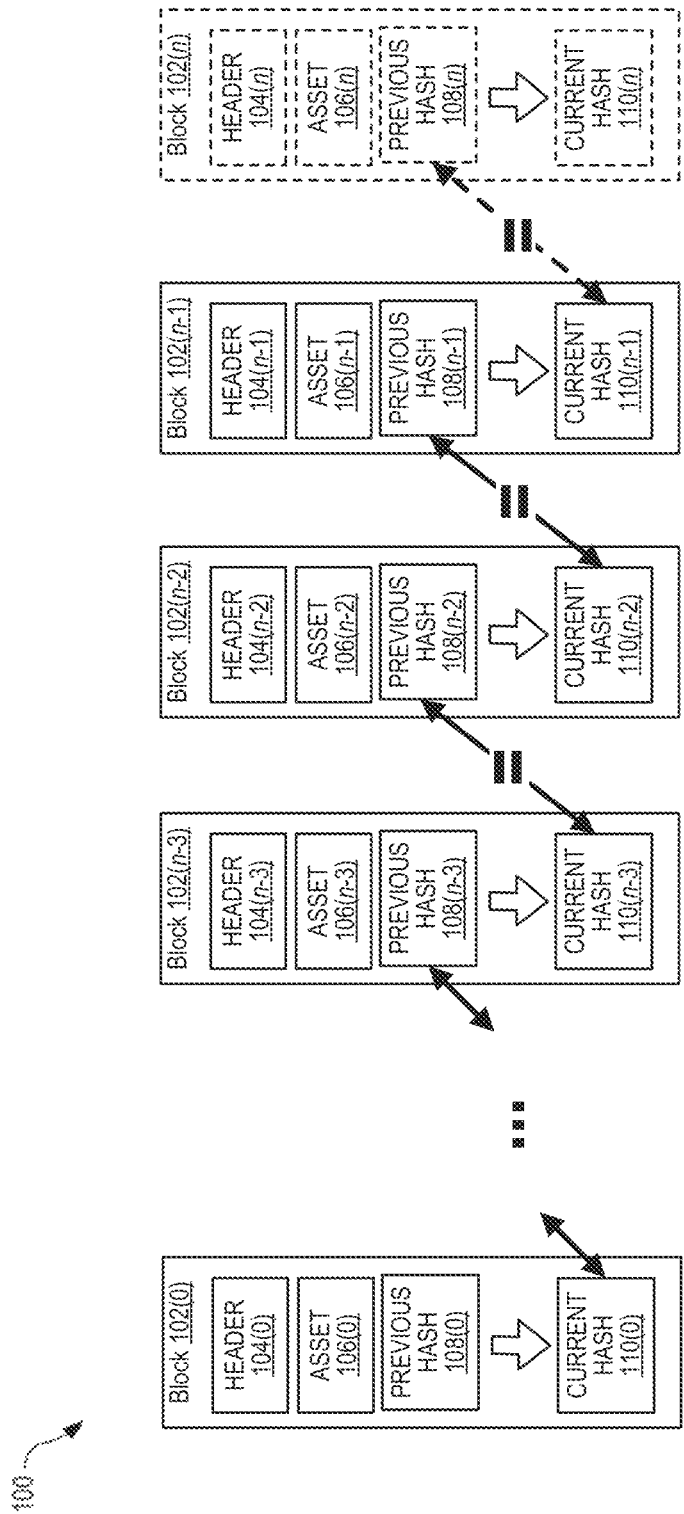
FIG. 1 shows a series of n blocks that are cryptographically linked to form a blockchain.

Various features of the technologies described herein will become more apparent to those skilled in the art from a study of the Detailed Description in conjunction with the drawings. Embodiments are illustrated by way of example and not limitation in the drawings. While the drawings depict various embodiments for the purpose of illustration, those skilled in the art will recognize that alternative embodiments may be employed without departing from the principles of the technologies. Accordingly, while specific embodiments are shown in the drawings, the technology is amenable to various modifications.

DETAILED DESCRIPTION

Advances in technology have resulted in ever increasing amounts of data in various industries. Oftentimes, these data are not only critically important but also are governed by increasing regulation of its ownership, exchange, and storage. These factors are driving the need for new solutions that allow data to be securely owned and shared in a manner that is traceable, revocable, and compliant with applicable regulations.

As an example, the convergence of innovations in health care, machine learning, and artificial intelligence have led to meaningful advances in personalized medicine. These advances have ushered in a new age in digital healthcare, where nearly everyone is able to readily access healthcare professionals, products, and services. In order to provide personalized medicine, data about patients must be examined. Tasks such as recommending an appropriate healthcare service (e.g., therapy) or prescribing an appropriate healthcare product (e.g., a pharmaceutical) rely on obtaining health-related data (or simply "health data") about patients. In particular, personalized medicine relies on analyses made not just using health data associated with the target patient but also using health data associated with tens, thousands, or even millions of other patients who have similarities to, and differences from, the target patient. Increasingly, these analyses also incorporate non-health data (broadly categorized as "life data") to make healthcare recommendations that will have the greatest likelihood of success given each patient's broader life circumstances. As a result, the value of health and life data is rapidly increasing, and many entities have developed (and continue to develop) products that act as sources of this data. Examples of such devices include consumer electronic devices, such as mobile phones and fitness trackers, and specialized medical equipment, such as insulin pumps, continuous glucose monitors, and implantable cardioverter defibrillators (ICDs).

Given the volume and value of health and life data, regulators and companies alike recognize the need to simultaneously: (i) protect such data from unauthorized use, (ii) share such data with a wide variety of "need-to-know" stakeholders, (iii) perform complex analytics, ML, and AI computations on such data, and (iv) maintain full regulatory compliance throughout all data-related activities. However, government regulations and corporate data handling policies vary widely, as do the data management solutions used to implement these regulations and policies. This complicates efforts by companies to securely access, share, and analyze health and life data in the provision of personalized healthcare services.

Traditional data management solutions—including on-premises and cloud-based solutions—have historically been used to provide some level of secure storage. However, these traditional data management solutions fail to fully address four areas of interest:

Data Security: Traditional data management solutions carry significant security vulnerabilities that are exploitable by unauthorized entities (also referred to as "attackers" or "hackers"), and therefore are susceptible to breaches in which health and life data is exfiltrated;

Data Ownership: New laws have begun requiring that owners have functional control over their data, and this can be difficult, if not impossible, to accomplish using traditional data management solutions; and Data Sharing: To ensure that data is exchanged securely, traditional data management solutions normally require direct integrations for transferring data from one repository to another. These "direct transfer" approaches present several challenges, however. Not only can it be difficult to implement these approaches at scale, but owners may only have control over the "transfer from" repositories and not the "transfer to" repositories, in which case the owners will lose functional control over their data.

Intelligence: Often, there is a substantial set of under-used or under-utilized data within an entity's datastores. The ability to leverage that wealth of untapped data is relegated to sophisticated entities that have spent years (and normally millions of dollars) in understanding this untapped data. Reasons for this include the inability to share data to internal groups and the limitations typically imposed to prevent exposure of this data. This becomes even more difficult if the untapped data is representative of, or related to, PII, PHI, Payment Card Industry Data Security Standard ("PSS DCI") information, or other sensitive information. Additionally, the ability to control data access for intelligence-related products means that entities can, and often do, keep a single source of truth; the traditional approach to creating new datastores that include "safe" or "sanitized"

copies of the data is no longer needed. As further discussed below, combining graph data structures with the underlying distributed ledger of a blockchain allows the data stored therein to be contextualized. This adds more intelligence to the data than would be provided by a tabular database.

In some more recent implementations, traditional data management solutions are coupled to a computer program (also called a "software application" or simply "application") that records certain data exchange activities on a blockchain for the purpose of providing some degree of transparency and auditability as to how data is being shared. In these implementations, the blockchain itself may dictate how data is allowed to be exchanged, and the blockchain may record the fact that an exchange has occurred even though the blockchain does not effect the exchange directly. The actual sharing of data between repositories still occurs as further described above, with all associated challenges.

Introduced herein is a computational architecture (also referred to as a "computational infrastructure") that addresses the limitations of traditional data management solutions using a highly secure data management solution coupled with consent-based sharing. At a high level, the computational architecture applies blockchain methodologies to both transaction data and business data, as further described below, such that both types of data are stored "on chain" in the same computational architecture. This enables several significant advantages over traditional data management solutions with respect to data security, data ownership, data sharing, and intelligence, as described herein.

The computational architecture can assign one or more owners to each individual data element. Such ownership can be enforced using blockchain methodologies similar to those used to assign ownership of a Bitcoin, but with additional flexibility to assign multiple co-owners and/or limited owners (also called "partial owners") of a data element. This differs from traditional data management solutions in which the administrator of the repository is the functional "owner" of the data stored therein and may control how such data is updated, deleted, and shared. Attackers need only gain access to this administrator's account to exploit the data within. In contrast, in the computational architecture described herein, administration is decoupled from ownership. While the administrator of the computational architecture may define specific data governance rules—such as, for example, a rule that the data element patient name shall be owned by patient—the administrator will not own the actual data element patient name when that data is recorded on the blockchain (and, by extension, the administrator will not have access to the data element patient name unless consented by the patient). This confers greater data security and control to the owner(s). The flexibility to assign single owner, multiple co-owners, and/or limited owners to a data element allows health-related companies to provide individuals with functional control over their data and comply with data privacy regulations while retaining the access necessary to run critical business operations.

The data involved in an exchange can be broadly categorized into two types. First, data describing various exchange events (generally referred to as "transaction data") may include data detailing the granting of access rights by an owner to a permissioned user (also called a "grantee"), the accessing of data by a grantee, the editing of access rights by an owner, and the revoking of access rights by an owner. These exchange events may be referred to as "consent events," "query events," "consent update events," and "revocation events," respectively. Each different type of transaction involves different sets of transaction data. Second, the specific data—generally called "business data"—that is shared during the exchange event may include a patient medical record, driver's license information, medical claim, step counts from a tracking device (also called an "activity tracker" or "wellness tracker"), geographical coordinates (e.g., generated by the Global Positioning System), and any other health or life data. In traditional data management solutions, transaction data and business data are stored in separate repositories, each repository being structured to store a specific type of data. This is referred to as "off-chain" data storage. In a traditional data management solution that is linked to a blockchain, the business data is stored in one or more "off-chain" repositories, while the transaction data is stored on the blockchain—that is, "on chain." In the computational architecture introduced herein, both transaction data and business data are stored "on chain," conferring several advantages over traditional data management solutions.

The computational architecture achieves consent-based sharing by implementing smart contracts between owners rather than through direct transfer approaches. The term "smart contract," as used herein, may refer to a self-executing contract with the terms of the agreement between the parties written into lines of code. The computational architecture may utilize multiple different types of smart contracts to effect different types of actions.

One example of a smart contract is a "consent contract" that enables owner(s) to share certain business data with other entities or groups of entities. These entities are called the "grantees" of the consent contract. Consent contracts may be advantageously used, for example, for exchange of business data between different stakeholders (e.g., between a patient and healthcare provider, or between a health insurance company and a healthcare provider). Importantly, because the business data in the computational architecture is consented from the owner to the grantee but is not physically transferred from one repository to another, the data remains under the owner's control even after the data is shared. This significantly improves data security and makes it easier to comply with regulations that require owners to retain control over their data.

In another embodiment, a smart contract referred to herein as a "consent contract update" enables an owner to change the parameters of a consent contract that has been previously created, thus updating the access rights of the grantee(s). The updated consent contract is added to the computational architecture and becomes the consent contract of record, while the previous consent contract is changed to a state of "archived." Thereafter, the grantee may access the consented business data in accordance with the updated consent contract. This differs from a traditional data management architecture in which changes to access rights must be implemented through a series of identity access management changes in combination with changes to application programming interfaces ("APIs") or 1:1 data integrations. In the computational architecture introduced herein, changes to a grantee's access rights can be made simply—for example, by executing a few lines of code—and put into immediate effect. This significantly simplifies the administrative processes required to securely operate large-scale networks in which hundreds, thousands, or even millions of users and application endpoints are constantly modifying the details of their data sharing preferences with each other. Consent contracts can be updated and then committed to the blockchain by a governance module (e.g., governance module 816 of FIG. 8).

One variation of a consent contract update is a "consent contract revocation," in which an owner changes the parameters of a consent contract that has been previously created so as to immediately terminate the consent contract, thus terminating the access rights of the grantee(s).

In another embodiment, a smart contract referred to herein as an "operations contract" may contain certain instructions that are automatically carried out when certain conditions or triggers are met. An operations contract may be advantageously used, for example, to search for patients who live within one mile of an oil refinery (in this case, the condition specifies a geographical area), and update the block containing the cancer screening recommendation of each patient from biannual to annual (in this case, the instruction specifies a new testing frequency).

Business data may be added to the computational architecture using create/read/update/delete and transfer ("CRUD+T") commands. Once validated by the network, a new block is created that stores the business data with inherent immutability and auditability. Importantly, the block containing the business data may also include, as part of the same block, the hash and signature of the block, the hash of the previous block, the cryptographic identifier ("ID") of the owner(s) of the business data, and various attributes related to the business data. Thus, the computational architecture may support CRUD+T operations in contrast to traditional blockchains. While create operations may already be inherent to the user, the other operations—namely, read, update, delete, and transfer—may need to pass through a governance module, as further discussed below.

The computational architecture herein differs from other blockchains in how transaction data and business data are structured on a block. Most blockchains pre-define a fixed set of data fields (or simply "fields") that are present on every block, a fixed schema (i.e., data structure) that data on the block must follow, and a fixed size for the block itself. This configuration works well for applications such as cryptocurrency, where all blocks on those blockchains can reasonably be expected to have identical fields, schemas, and size. However, in applying a blockchain to a complex data network, this fixed approach would significantly constrain the network's ability to store diverse types of data. In contrast, the computational architecture introduced herein allows each block to vary from other blocks in terms of fields, schemas, and size. Said another way, the blocks are dynamic in the sense that they may be configurable in terms of field count, schema, or field size. In this way, the blockchain is able to store a variety of different types of data "on chain," with each block potentially varying from others on the blockchain. By way of example, one block may store a patient's name and birthdate, another block may store a photo of the patient's driver's license, and a third block may store the patient's recent lab result. These three blocks may differ in terms of field count, schema, or field size so as to accommodate the data to be stored therein.

The computational architecture introduced herein achieves this variability by treating the data within each block as an autonomous unit of information called a "smart data object." At a high level, the smart data object wraps the asset (i.e., the data) with information related to, for example, its own security, data structure, and ownership. These "layers" serve as the smart data object's properties for existence within the blockchain. In this way, a single blockchain is able host a heterogenous set (also called a "chain") of blocks with different configurations, yet those blocks may interact under consent contracts as discussed herein. At the core of the smart data object is the actual data itself. This is akin to a digital record in a relational database management system ("RDBMS") or a document in a NoSQL system. This data can be stored in various ways. For example, the computational architecture stores the data in as a JavaScript Object Notation ("JSON") document in some embodiments.

Each entity that interacts with the blockchain managed by the computational architecture may be associated with an ID pair, which may be representative of a public and private key, identity, or address. These keys, identities, or addresses provide both identity—albeit anonymously or pseudonymously—and authorization to act on the data within the blockchain. To manage these ID pairs, the computational architecture may support a digital wallet that associates ID pairs with authentication credentials that can be used to access the computational architecture.

Each block is an autonomous unit regardless of the blockchain to which it belongs, as well as autonomous from the preceding and superseding block. Each block may embed unique information regarding (i) permissions, (ii) attributes, (iii) ownership, (iv) edge relationships, and (v) metadata, as further discussed below. This information may be visible to grantees who are representative of permissioned users of the computational architecture, though it may not be editable once stored within the blockchain.

Normally, the structure of the asset of the smart data object is defined by the designer, and users of the blockchain may simply be required to adhere to the defined schema. The metadata layer may allow users to add additional information about the data per block. For example, this information may relate to the original source (e.g., an Internet Protocol address for a computing device). This section may not always be necessary, and thus may not be included in some embodiments of the smart data object. However, the metadata layer provides flexibility that users can take advantage of.

Each asset (e.g., block or smart data object) may be stored in a blockchain. Accordingly, the blockchain composition may place a "new" asset into a different "branch" from the origin block. This "branch" effectively becomes a sidechain for managing the corresponding asset over its lifecycle. The ability to maintain an asset-based sidechain can improve throughput to the blockchain, for example, via consensus and persistence operations. Additionally, this approach ensures that the asset cannot be double-spent due to the sidechain acting in accordance with the same protocols as the blockchain but in a smaller capacity. A sidechain can also be pruned from the full blockchain without implicating any other sidechains or the full blockchain. This may be helpful—and, in some instances, necessary—to adhere to regulations related to data management such as the General Data Protection Regulation ("GDPR"), Health Insurance Portability and Accountability Act ("HIPAA"), and Part 11 Regulations issued by the US Food and Drug Administration ("FDA").

As noted above, most traditional blockchain implementations store transaction data "on chain" in non-optimized or indexed flat files and store business data "off chain" with just a hash value that is representative of the business data being "on chain." In this scenario, the search of a block or piece of data on a flat file storage would be linear and classified as O(n). This is sufficient for use cases that do not require generalized query and/or analytics of information stored in the blocks. However, if the user wishes to analyze the on-chain transaction data together with off-chain business data, a two-step data gathering and validating effort would be required. Users generally prefer that transaction data and business data be co-located, since co-location provides a richer data experience and renders the two-step process unnecessary since the data is no longer located in two places. Additionally, users benefit from having the immutability, auditability, and ownership features of blockchain apply equally to transaction data and business data. By (i) implementing a graph model instead of flat files and (i) co-locating business data and transaction data in an on-chain graph format, the computational architecture introduced herein provides additional analytical insights and allows users to perform complex queries, business operations, and analytics of transaction data and business data at the same time. In this scenario, the user can employ b-tree indexing strategies wherein data searches are classified as O(log n).

There are some situations where data stored on the computational architecture (and, more specifically, stored or referenced in the blocks of the blockchain) is most useful when considered in combination with, or in context to, other data stored on the computational architecture. Assume, for example, that information regarding procedures involving different patients is stored on the computational architecture, and that there is a recall for a healthcare product used in some of those procedures. Rather than parse individual blocks to determine which procedures involved the recalled healthcare product, the computational architecture may instead establish relationships between these procedures to enable contextualization of the healthcare product data, together with patient data, to enable deep analytics and end-to-end traceability in a manner that traditional data management solutions cannot accomplish. Accordingly, upon receiving input indicative of a criterion (e.g., involving the recalled healthcare product), the computational architecture may be able to identify those procedures that have been programmatically associated with one another due to having the criterion in common. As further discussed below, such an approach allows the data stored on the computational architecture to be readily searchable (and thus digital records of interest to be readily discoverable).

Understanding the relationships between different assets can be quite difficult, however. Introduced here is an approach to combining two technologies—a graph database and blockchain—in such a way that implicit and explicit relationships between disparate data can be established while maintaining the security and privacy parameters applicable to such data. To accomplish this, a graph modeling module can determine the relationships between data stored in various blocks of one or more blockchains. As further discussed below, the graph modeling model can accomplish this by applying the rules codified in a data structure referred to as a "dictionary" and/or applying ML or AI algorithms that are trained to learn how to discover these relationships. These relationships can then be represented in the form of graph models. At a high level, these graph models associate blocks that provide context to other blocks in the blockchain(s).

The computational architecture discussed below with reference to FIGS. 1 and 3-20 can be used to graphically model the relationships between data on one or more blockchains. The computational architecture represents a complex set of constructs, network nodes, protocols, and functions that collectively create a data storage platform that is auditable, immutable, and contextualizable.

Approaches to learning the relationships between data stored on a computational architecture and producing visual representations (also referred to as "visualizations") of those relationships are also introduced herein. Referring again to the above-mentioned example, the computational architecture may identify a series of digital records that satisfy a criterion (e.g., involve the recalled healthcare product) that is provided as input. In this situation, the computational architecture can create a visualization for each digital record that has context built into it. Then, the computational architecture can "stitch" the series of visualizations together to illustrate how the series of digital records relate to one another.

As further discussed below, one approach to determining the relationships between various data is to perform automated analysis—for example, with ML or AI algorithms—on graph models produced for different entities. An entity could be, for example, a person, product, or place. These graph models may be helpful in understanding entities from a more comprehensive perspective. Assume, for example, that data related to a patient that underwent a surgical procedure is stored in various blocks on a blockchain. These various blocks may include information regarding the patient (e.g., name, date of birth, weight, prescriptions), the surgical procedure (e.g., date and time, products used, outcome), the healthcare professional who performed the surgical procedure, the healthcare facility at which the surgical procedure was performed, and the like. Interrelating these pieces of information through a graph model not only provides a more holistic view of the surgical procedure, but also allows insights to be surfaced more quickly. As an example, all surgical procedures involving the healthcare professional could be easily identified if the corresponding graph models are interconnected to one another through the graph node corresponding to the healthcare professional.

As noted herein, the computational architecture allows business operations, including complex queries, analytics, and ML or AI algorithms, to be applied directly to on-chain data without the need to download or restructure the data. In one embodiment, the business operations may consist of applying a set of business rules to the on-chain data to perform a workflow or set of automated tasks. By way of example, a complex query may be performed to identify patients who are (i) uninsured, (ii) female, and either (iii-a) are currently pregnant and have an adjusted income of less than $2,000 per month or (iii-b) are not pregnant and have an adjusted income of less than $1,000 per month. If the query returns matching patient data, a workflow can be automatically initiated whereby a Medicaid application is pre-filled with the patient's information and submitted to her state Medicaid agency for enrollment.

In another embodiment, the business operations may consist of analyzing the on-chain data to identify relationships and patterns. By way of example, an AI engine may query the on-chain data to analyze the relationships between doctors whose surgical patients have a lower-than-average infection rate. In this example, the AI engine may find that these doctors tend to use a particular brand of suture and that their patients tend to walk 20 percent more steps in the week following surgery. In response to these insights, the AI engine may implement or recommend changes to the surgical supply list and changes to patients' post-operative care plans.

The utilization of a graph model in this computational architecture provides significant benefits that cannot be realized through traditional data management. In particular, a graph model defines explicit relationships between individual assets. In this computational architecture, each individual asset may equate to one "graph node," and each graph node may equate to a single block on the blockchain. The explicit relationship between two graph nodes can be defined and stored as an attribute within the blocks. Machine learning may be applied to identify additional relationships that are not explicitly defined but can be inferred based on the nature of the data. These inferred relationships may be called "implied relationships." Lastly, each block can contain a hash value and the previous block's hash. These hashes establish relationships between a block, its predecessor(s), and its descendant(s). In this way, the computational architecture establishes multiple layers of relationships between data—both business data and transaction data. These relationships may be analyzed and visualized together with the data itself to gain deeper insights for the purpose of optimizing processes, systems, engagements, and more.

By way of example, an ML algorithm may be applied to the computational architecture, as more fully described below, wherein the ML algorithm is trained to identify data that fall within a certain similarity threshold. As a specific example, the data asset first_name="Jonathan" and related data asset last_name="Clarksen" may be determined to be similar to data asset first_name="Johnathan" and related data asset last_name="Clarkson." Once similar data are identified by the ML algorithm, an implied relationship may be created between Jonathan Clarksen and Johnathan Clarkson. Further, a business operation, as more fully described below, may be initiated to communicate with a user to seek additional information that would validate whether Jonathan Clarksen and Johnathan Clarkson are the same individual. If the results of that business operation validate that Jonathan Clarksen and Johnathan Clarkson are definitively the same person, an operations contract, as more fully described below, may be initiated to create an explicit relationship between data associated with Jonathan Clarksen and data associated with Johnathan Clarkson. In this manner, the computational architecture makes it possible to combine and automate a series of complex tasks that would, in a traditional data management system, require several independent and manually orchestrated actions that are prone to error.

Additionally or alternatively, an ML algorithm could be applied to the computational architecture to establish explicit relationships between disparate assets without the need for a validation workflow as described in the preceding example. In an embodiment, a consent contract may be applied to demonstrate mechanisms by which relationships may be established between assets owned by different owners, though this is not required and the same relationships may be demonstrated without the use of consent contracts. By way of example, a first researcher ("Researcher A") may own assets comprised od detailed historical weather patterns at specific latitude and longitude coordinates ("lat/long coordinates"). A second researcher ("Researcher B") may own assets comprised of emergency room ("ER") visits by facility and clinical diagnoses codes associated with such ER visits. Researcher A may execute a consent contract granting Researcher B permission-based access to the weather-related assets. Researcher B may access the consented weather-related assets and apply an ML algorithm thereto, so as to correlate lat/long coordinates with ER facility addresses that are within ten miles of the lat/long coordinates, for example. After correlations are identified, the ML algorithm may execute an operations contract to establish an explicit relationship between lat/long coordinates and ER facility addresses. These explicit relationships could be added as a new edge relationship in a block (e.g., data block 302 of FIG. 3 or graph data block 1002 of FIG. 10) and added to the blockchain as an update operation to the previous block. The updated block with one or more newly added edge relationships may have a different owner ID (e.g., owner ID 316 of FIG. 3) than the previous block. In this example, the updated block may be co-owned by Researcher A and Researcher B. After explicit relationships are formed between the weather-related assets and ER-related assets, the ML algorithm can use these explicit relationships to quickly identify spikes in particular diagnosis codes during specific types of weather events (e.g., an increase in patients presenting with acute renal failure during high-heat weather events). In this manner, the computational architecture can simplify the process of applying ML and AI to form explicit relationships between assets, including in cases where assets are owned by different owners (and therefore have different owner IDs), and use those explicit relationships to identify insights across disparate assets that would otherwise be very difficult to discern. Accordingly, the computational architecture may be used to simplify the process where owners (e.g., researchers) collaborate in a many:many capacity, working collectively to discover insights that would be very difficult to discover through one:one collaborations. This type of many:many collaboration may be used as the basis for neural networks and other types of swarm intelligence.

In another embodiment, an ML algorithm may be applied to the computational architecture to identify, create, query, or analyze relationships between assets that have certain attributes in common, where such relationships are not predetermined. By way of example, a user may access, either via ownership or via consent contract, assets on the computational architecture representing disparate data elements related to various surgical encounters: patients, surgeons, procedure codes, diagnosis codes, patient outcomes, surgical supplies, and supply costs. The inherent relationship between a surgical encounter and the data elements comprising that surgical encounter may be generally known to the user, and in a traditional tabular data model, these known relationships would be represented as joins between tables (e.g., "encounter" table and "patient" table are joined by data element patient_ID). In contrast, using the computational architecture introduced herein, known relationships can be defined using edge relationships between individual data assets rather than joins between tables. In this example, the user may define known relationships (i.e., explicit relationships) as one or more edge relationships in a block (e.g., data block 302 of FIG. 3 or graph data block 1002 of FIG. 10). Through these edge relationships, the disparate elements related to various surgical encounters are now interconnected through first order (e.g., Patient A-to-procedure code 123), second order (e.g., Patient A-to-procedure code 123-to-Patient B), and $n^{th}$ order (e.g., Patient A-to-procedure code 123-to-Patient B-to-Surgeon C-to- . . . ) relationships.

Importantly, in a tabular data model, all relationships (i.e., joins) must be understood and defined at the data persistence layer in order for queries to operate efficiently. A query in a tabular data model might request, "give me all the data representing the path between Patient A and Patient B." If Patient A and Patient B are not directly connected by any joins in the table, the query will return a null response. Importantly, the query must identify all possible permutations of all possible $n^{th}$-order relationships in order to return the desired result. For higher order queries, this drastically decreases the efficiency of the query to the point of being functionally impossible to execute. In contrast, the computational architecture introduced herein allows the user to simultaneously query relationships (e.g., edge relationships 1032 of FIG. 10) and data (e.g., data 1024 of FIG. 10), wherein such query seeks to discover whether there is any relationship between two seemingly unrelated data assets (i.e., "is there a path between Patient A and Patient B?"). Although no predefined path may exist between Patient A and Patient B, the computational architecture may return a result showing an $n^{th}$-order relationship between Patient A and Patient B, for example, where procedure code 123, Surgeon C, and supply X are all commonalities between the two patients. In short, whereas the tabular data model has no functionally workable mechanism to extrapolate new relationships based on analysis of data elements across multiple tables, the computational architecture introduced herein is able to easily analyze unrelated assets and return new $n^{th}$-order relationships to the user.

Building further on the same embodiment, the ML algorithm may be applied to perform this type of relationship analysis at scale, across hundreds, thousands, millions, or even billions of assets. The ML algorithm may be trained to discover patterns or commonalities among patients who underwent similar procedures and experienced favorable patient outcomes. Using the computational architecture herein, the ML algorithm does not need to be told every possible permutation of every possible commonality; it may search the entire graph to identify such commonalities. By way of example, the ML algorithm may analyze millions of assets relating to patients, surgeons, procedure codes, diagnosis codes, patient outcomes, surgical supplies, and supply costs, and identify that, for patients who underwent procedure code 123 and experienced favorable patient outcomes, Surgeon C and supply X were commonalities in a majority of those encounters. Further, a user may apply a business rule to create an implied relationship between patients sharing these commonalities, or execute an operations contract to add a new patient-to-patient edge relationship (e.g., edge relationship 1032 of FIG. 10) to a block (e.g., graph data block 1002 of FIG. 10), thus dynamically creating a group, or cohort, of similarly situated patients. In this manner, the computational architecture differs significantly from tabular data models in its ability to simultaneously analyze data attributes and $n^{th}$-order relationships, identify commonalities between unrelated data, derive new implied and explicit relationships, and use these insights to modify business processes.

Another possibility of the use of an ML algorithm with the network of data supported by the computational architecture that represents patients, surgeons, diagnosis, procedure codes, diagnosis codes, patient outcomes, surgical supplies, and the like. Hospitals already understand obvious relationships between a surgery case and the various parts of it (e.g., the surgeon, patient, surgical supplies, etc.). But the information is usually limited to the relationships of a single surgical case. By defining these known relationships as edges (e.g., by documenting as edge relationships 1032 of FIG. 10) and then populating nodes that are representative of the corresponding data, a set of separate graphs appear. But as the common providers and cases are tied together such that a network of intertwined surgical cases may emerge. Applying an ML algorithm to classify surgical cases and outcomes may allow for surfacing or highlighting of relationships on success of certain patient demographic patterns and surgical techniques. These relationships between identified similar surgical cases can then be "drawn" with new edges in a graph. This allows users to extrapolate improved outcomes based on data. While this is something that is derived from the data, and therefore could arguably have come from a database, relationships in a graph allow other algorithms to derive insights that are difficult, if not impossible, obtain through analysis of tables.

These types of complex operations benefit from a computational architecture that can perform at very high speeds. Most traditional blockchains, particularly cryptocurrency blockchains, add new blocks at relatively slow speeds. By way of example, the time it takes to add a new transaction block to the Bitcoin blockchain can vary based on various factors, but could be as long as ten or more minutes. Users expect much faster "create" operations for assets, as it is desirable for assets to be immediately available (e.g., for sharing) in some scenarios. To address this, the computational architecture introduced herein may replace a Proof-of-Work algorithm with a Proof-of-Authority ("POA") algorithm. Note that POA algorithms may also be called Modified Proof-of-Stake ("mPOS") algorithms. This POA algorithm relies on the integrity of a given network node in the network. If the network node acts in a responsible manner (e.g., does not introduce "bad" assets, vote for "bad" assets, or fail to participate) its integrity score remains intact. Acting irresponsibly may negatively impact the integrity score of the network node. At a certain threshold integrity score, the network node may no longer allowed to participate in the network and will be explicitly ignored. Said another way, the network node may not be permitted to participate in blockchain operations if its integrity score falls beneath a certain threshold. In this manner, the computational architecture is able to dramatically increase the throughput of transactions on the network since creation of a block on the network does not require mining of a nonce.

The capabilities of the computational architecture described herein provide a method for health-related entities to exchange data in a simple and compliant manner and apply business operations to that data without compromising the secure, compliant storage of that data. This is especially critical for businesses that need to access, share, and analyze data that is subject to HIPAA, GDPR, and other data privacy regulations.

This computational architecture enables health-related entities to provide personalized patient care by making health and life data available, for example, to analytical tools and services that are able to surface deeper insights than would be possible with traditional data management systems, and take action based on those insights in an automated manner. Examples of health-related entities include providers (e.g., healthcare systems, healthcare facilities, and healthcare professionals), payers (e.g., insurers), pharmaceutical companies, and the like. With this computational architecture, health-related entities can readily connect with each other, share data in a compliant manner using consent-based data sharing, and analyze that data as if that data were aggregated into a single system.

Terminology

References in the present disclosure to "an embodiment" or "some embodiments" mean that the feature, function, structure, or characteristic being described is included in at least one embodiment. Occurrences of such phrases do not necessarily refer to the same embodiment, nor are they necessarily referring to alternative embodiments that are mutually exclusive of one another.

The term "based on" is to be construed in an inclusive sense rather than an exclusive sense. That is, in the sense of "including but not limited to." Thus, unless otherwise noted, the term "based on" is intended to mean "based at least in part on."

The terms "connected," "coupled," and variants thereof are intended to include any connection or coupling between two or more elements, either direct or indirect. The connection or coupling can be physical, logical, or a combination thereof. For example, elements may be electrically or communicatively coupled to one another despite not sharing a physical connection.

The term "module" may refer broadly to software, firmware, hardware, or combinations thereof. Modules are typically functional components that generate one or more outputs based on one or more inputs.

When used in reference to a list of multiple items, the word "or" is intended to cover all of the following interpretations: any of the items in the list, all of the items in the list, and any combination of items in the list.

Overview of Computational Architecture

FIG. 1 shows a series of n blocks 102 that are cryptographically linked to form a blockchain 100. Each block 102 stores header information 104, an asset 106, a previous hash value 108, and a current hash value 110. When cryptographically linked, the blocks 102 form an ordered sequence in which each block is uniquely indexed. For clarity, each block 102 is labeled with an index in parentheses that identities the position of that block 102 in the blockchain 100. For example, the $i^{th}$ block 102 is labeled block 102(i), and it stores similarly indexed header information 104(i), asset 106(i), previous hash value 108(i), and current hash value 110(i). As shown in FIG. 1, the blockchain 100 begins with an origin block 102(0). The number of blocks in the blockchain 100 may be thousands, millions, or more. In FIG. 1, only the origin block 102(0) and the four most recent blocks 102(n−3), 102(n−2), 102(n−1), and 102(n) are shown.

Identical copies of the blockchain 100 may be stored on multiple computing nodes (or simply "nodes") that cooperate as a peer-to-peer distributed computing network to implement the blockchain 100 as a type of distributed ledger. In this case, the nodes cooperate to add new blocks to the blockchain 100 in a decentralized manner. Said another way, the nodes may cooperate to add new blocks to the blockchain 100 without a central authority or trusted third party.

A consensus protocol may be implemented by the nodes to validate data to be appended to the blockchain 100. Once data is validated by a node, the node may broadcast the validated data to all other nodes, which then update their local copies of the blockchain 100 by appending the validated data to the blockchain 100 as a new block. Validation may be implemented via proof of work (POW), POS, POA, or another type of consensus protocol. Once a block 102 is added to the blockchain 100, it can only be modified via collusion of a majority of the nodes (i.e., a 51 percent attack). Such collusion is highly unlikely—especially for private blockchains—so blockchains are considered secure by design.

Fundamentally, the blockchain 100 may be similar in some respects to those implemented for cryptocurrencies, such as Bitcoin and Ethereum, that process and then store data related to financial transaction. However, the blockchain 100 (and, more specifically, the asset 106 in each block 102) may be able to store any type of data. For example, the asset 106 may include protected health information ("PHI") or personal identifiable information ("PII") that are encrypted. Generally, PHI includes any information about the health status (also referred to as the "health state") of a person, healthcare products and services provisioned to the person, or payments made for healthcare products and services. This information may be generally referred to as "medical data." For medical data to be considered PHI, it must include at least one identifying piece of information. Thus, PHI includes medical data and PII. Examples of PII include name, social security number, and date of birth. In some embodiments the asset 106 is fully unencrypted, while in other embodiments the asset 106 is fully encrypted. Alternatively, the asset 106 may be partially unencrypted and partially encrypted. Advantageously, data that is stored in the blockchain 100 may essentially be immutable, and thus can be readily verified during an audit.

While not shown in FIG. 1, the blockchain 100 may have a unique name or identifier that allows it to be uniquely identified from amongst other blockchains that are stored, implemented, or managed by the same computational architecture. Thus, the blockchain 100 may not be the only one accessible to the computational architecture.

FIG. 1 also illustrates how when a new block 102(n) is added to the blockchain 100, it can be cryptographically linked to the previous block 102(n−1). The current hash value 110(n−1) of the previous block 102(n−1) is copied and then stored as the previous hash value 108(n) of the new block 102(n). Thus, the current hash value 110(n−1) equals the previous hash value 108(n). The current hash value 110(n) can then be determined by hashing the header information 104(n), asset 106(n), and previous hash value 108(n) stored in the new block 102(n). For example, the header information 104(n), asset 106(n), and previous hash value 108(n) may be concatenated into a single string that is input into a cryptographic hash function (or simply "hash function") whose output is stored as the current hash value 110(n). Alternatively, the header information 104(n), asset 106(n), and previous hash value 108(n) may be pair-wise hashed into a Merkle tree whose root node is stored as the current hash value 110(n). Other ways of using the hash function to generate the current hash value 110(n) may be employed without departing from the principles of the present disclosure. Each hash value may be representative of a cryptographically calculated value of fixed length. While the hash values are not guaranteed to be unique across all data, it is usually very hard to duplicate so hash values are valuable in identifying blocks within the blockchain.

The current hash values 110 provide an efficient way to identify changes to any data stored in any block 102, thereby ensuring both the integrity of the data stored in the blockchain 100 and the order of the blocks 102 in the blockchain 100. To appreciate how the current hash values 110 enforce data integrity and block order, consider a change made to one or more of the header information 104(i), asset 106(i), and previous hash value 108(i) of the block 102(i), where i is any integer between 1 and n. The change may be detected by rehashing the block 102(i) and comparing the result with the current hash value 110(i) stored in the block 102(i). Additionally or alternatively, the rehash value may be compared to the previous hash value 108(i+1) that is stored in the subsequent block 102(i+1). Due to the change, the rehash value will not equal the current hash value 110(i) and the previous hash value 108(i+1). These unequal hash values can be used to identify an attempt to alter the block 102(i). Assuming no entity controls a majority of the voting power (i.e., there is no collusion), such attempts to modify data in the blockchain 100 will be rejected due to the consensus protocols described above.

The blockchain 100 may be verified via two steps. First, for each block 102(i), a recomputed hash of the header information 104(i), asset 106(i), and previous hash value 108(i) may be compared to the current hash value 110(i) to ensure that the rehash value equals the current hash value 110(i). This first step authenticates the data stored within each block 102. Second, for each block 102(i), the previous hash value 108(i) may be compared to the current hash value 110(i−1) of the previous block 102(i−1) to ensure that these values are equal. This second step authenticates the order of the blocks 102. Verification of the blockchain 100 may proceed "backwards." Said another way, the blockchain 100 can be verified by sequentially verifying each block 102 starting from the most recent block 102(n) and ending at the origin block 102(0). Alternatively, verification may proceed "forwards" by sequentially verifying each block 102 starting from the origin block 102(0) and ending with the most recent block 102(n). Validation may occur periodically (e.g., once per hour, day, or week), in response to a predetermined number of new blocks being added to the blockchain 100, or in accordance with a different schedule or triggering event. For the origin block 102(0), the previous hash value 108(0) may be set to an arbitrarily chosen value.

In FIG. 1, each block 102(i) is shown storing its current hash value 110(i). However, it is not necessary for each block 102(i) to store its current hash value 110(i) since it can always be generated by hashing the other data stored in the block 102(i). Nevertheless, storing the current hash value 110(i) in each block 102(i) can greatly speed up retrieval of the blocks 102, and thus access to the asset 106, by using the current hash values 110 as search keys in a database index. For example, each current hash value 110(i) may be represented as a node in a binary search tree (e.g., a B-tree, self-balancing binary search tree, or fractal tree index). Each node may also store the corresponding index i. When a new block 102(n) is added to the blockchain 100, its owner (e.g., as indicated by the owner ID 216 of FIG. 2) may be given the resulting current hash value 110(n) as a confirmation. When the owner wishes to subsequently retrieve the corresponding asset 106(n) from the blockchain 100, the owner may submit a request that contains an indication of the confirmation (e.g., the current hash value 110(n) that serves as a unique identifier). The binary search tree can be searched to quickly find the index n. The block 102(n) may then be directly accessed without having to sequentially search the blocks 102. As an additional check, the receipt may be compared to the current hash value 110(n) of the retrieved block 102(n) to ensure the values match.

Overview of Conventional Blockchain Implementations

Figure 2A:
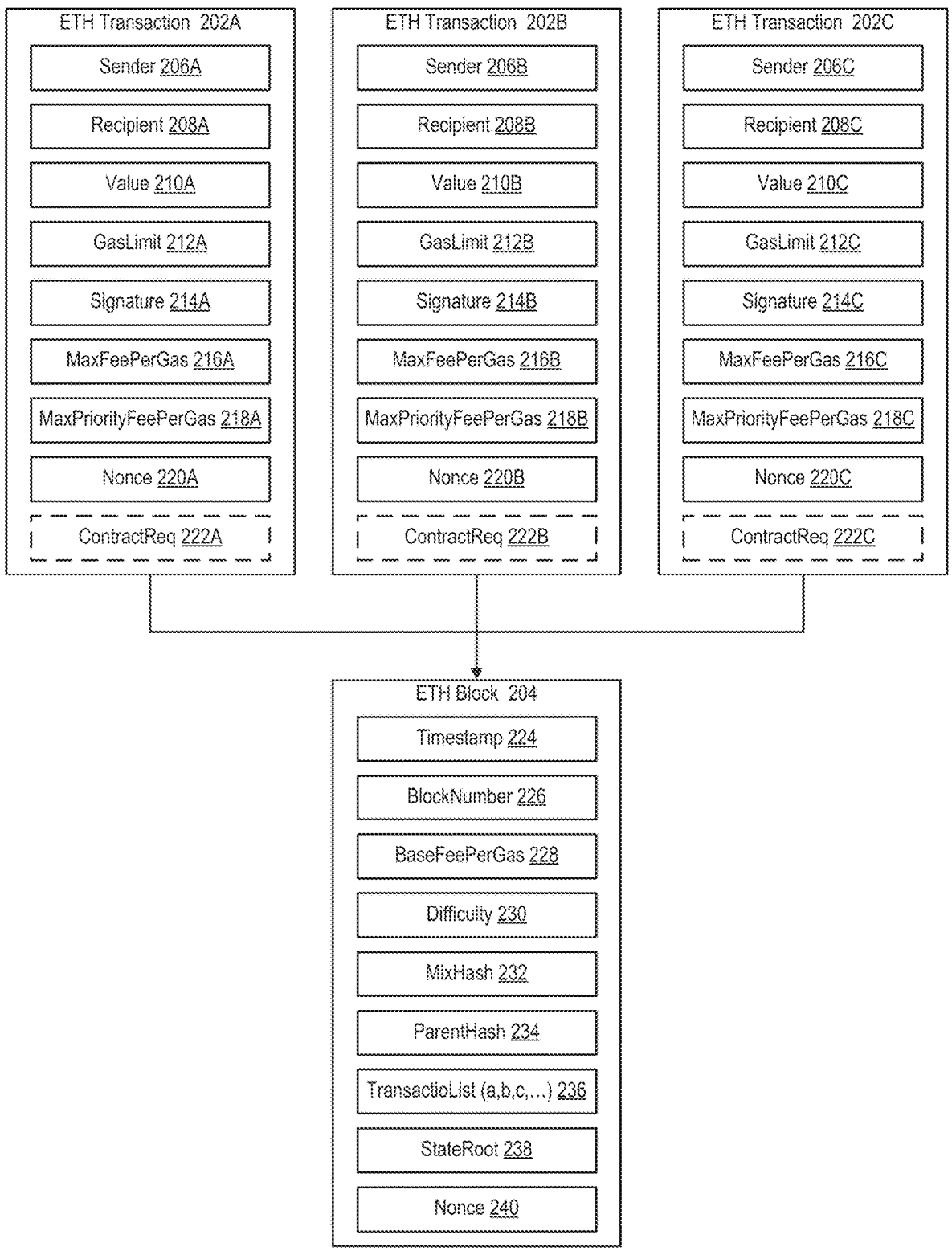
FIG. 2A illustrates a typical Ethereum block structure.
Figure 2B:
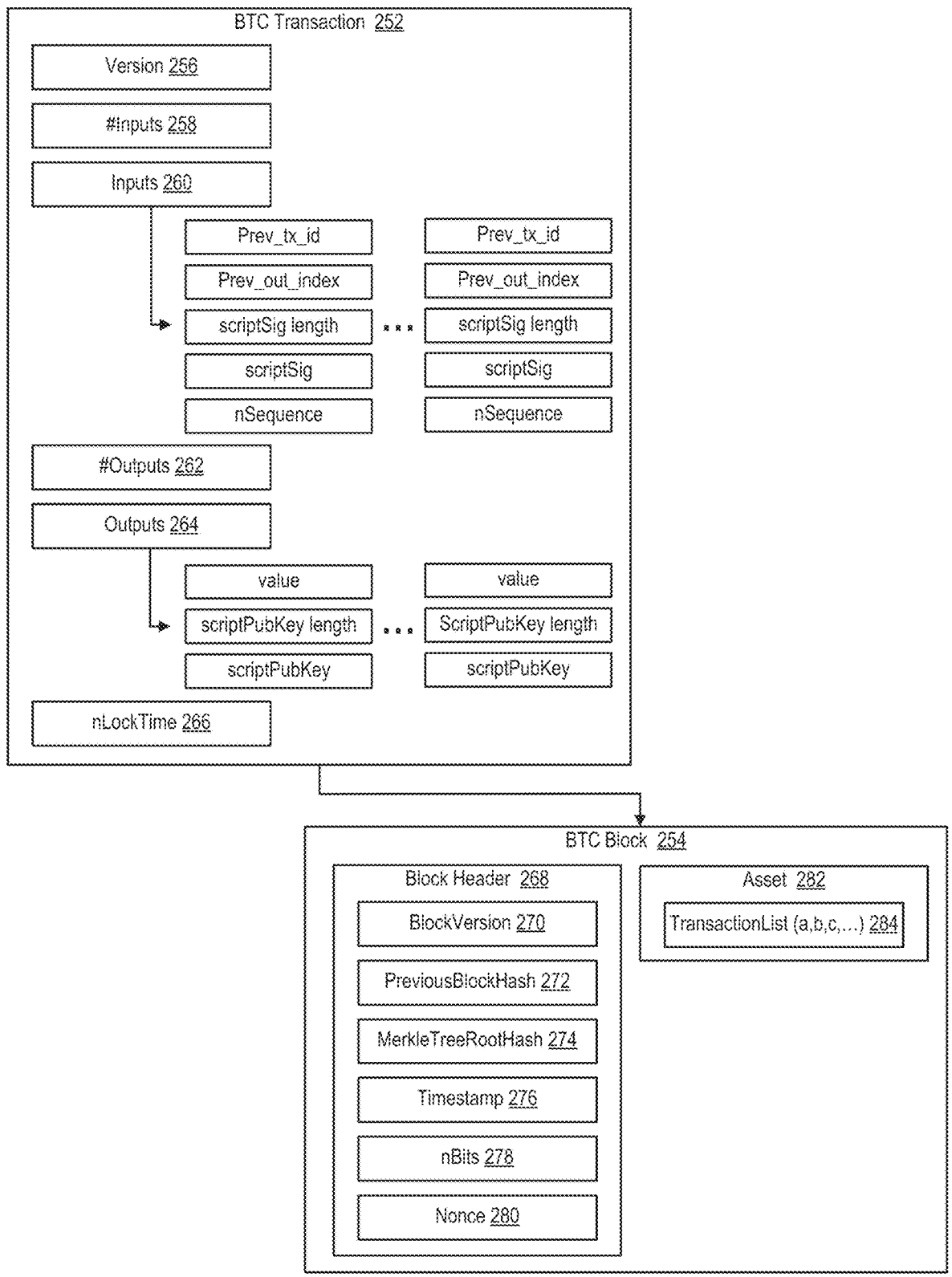
FIG. 2B illustrates a typical Bitcoin block structure.

FIGS. 2A-B illustrates examples of block structures in conventional blockchain implementations. Specifically, FIG. 2A illustrates the block structure used by Ethereum, while FIG. 2B illustrates the block structure used by Bitcoin. In both cases, each transaction has a fixed set of information that describes the transaction and, therefore, each block stores a fixed set of information using a fixed structure. In the case of Ethereum shown in FIG. 2A, a transaction 202A-C generates the following transaction information: a sender 206A-C, a recipient 208A-C, a value 210A-C, a gas limit 212A-C, a signature 214A-C, a max fee per gas 216A-C, a max priority fee per gas 218A-C, and a nonce 220A-C.

Optionally, an Ethereum transaction may also contain contract requirements 222A-C in the case that the transaction effects the creation of a smart contract, such as the minting of a new Ethereum token. Transaction information for multiple transactions 202A, 202B, and 202C are bundled together and then stored on a single Ethereum block 204. The Ethereum block 204 has a fixed set of fields, each of which require adherence to a prescribed data structure. Specifically, the Ethereum block 204 includes a timestamp 224, a block number 226, a base fee per gas 228, a difficulty 230, a mix hash 232, a parent hash 234, a state root 238, and a nonce 240. The Ethereum block 204 also contains a list of transactions 236 comprised of the transaction fields listed above.

The structure of the Ethereum block 204, the number of available fields, and the data types that can be entered into those fields tend to be fixed. However, the overall block size may vary depending slightly on the number of transactions stored in the list of transactions 236 and whether or not any of those transactions include contract requirements 222A-C.

FIG. 2B illustrates the Bitcoin transaction and block structure, which bears similarities to the Ethereum structure described above. The Bitcoin transaction 252 is comprised of a version 256, #inputs 258, inputs 260, #outputs 262, outputs 264, and nLockTime 266. Transaction information for multiple transactions are bundled together and stored on a single Bitcoin block 254. Inputs and outputs vary based on the transaction type or smart contract requirements. The Bitcoin block 254 has a fixed set of fields, each of which require adherence to a prescribed data structure. The block header 268 contains a block version 270, a previous block hash 272, a Merkle tree root hash 274, a timestamp 276, nBits 278, and a nonce 280. The block asset 282 contains a list of transactions 284 comprised of the transaction fields listed above.

In the example blockchains provided in FIGS. 2A-B, the block asset can only be comprised of the aforementioned set of fields, and it must adhere to a fixed structure in order to be successfully added to the blockchain. Other implementations of blockchains have been introduced that modify the block asset so as to accept a different type of data, such as replacing a list of transactions with "first_name, last_name" with a fixed format of "text string" but even in these cases, the block asset still predefines and enforces a fixed set of fields and a fixed data structure. That is, all block assets on the blockchain must store "first_name, last_name." in text format.

The fixed block configurations employed by most blockchains, including the examples provided in FIGS. 2A-B, impose a significant restraint on the utility of those blockchain for more complex use cases. A fixed configuration blockchain cannot be extended to accept new types of data; it must store the new data type on a wholly separate blockchain or deconstruct and rebuilt itself in a new configuration acceptable to the new data type. The former constricts the blockchain's use for complex query and analysis, while the latter compromises the integrity of the blockchain. In contrast, the computational architecture introduced herein treats each block on the blockchain as an autonomous unit of information that is called a "smart data object". At a high level, this self-contained unit wraps the asset (i.e., the data) with additional information that serve as properties for existence within the blockchain.

Cryptographic blockchains simply persist transaction as flat files on a node. These flat files are simply organized in chronological order of transactions that are adjudicated to the blockchain. These files are not necessarily supported for queries that data consumers are used to with enterprise databases and datastores. To find transactions—other than my transaction identifier—developers will take the flat filed from a compute note or storage node and persist that data into a lightweight database (e.g., RocksDB) that allows for queries of any data element within a block or transaction.

In contrast, the approach introduced here for storing data "on chain" with the use of document storage engines produce consistent storage behavior and provide the ability to query data much like a traditional database or datastore. As further discussed below, the data can vary for the "asset" or raw data that a smart data object encompasses. As part of a smart data object, the relationships of that smart data object to other smart data objects can be "fused" within the cryptographically sealed data structure. Efforts were previously made to produce graphs post-persistence in an effort to improve visualization of the underlying data. Conversely, the computational architecture introduced herein can utilize graph theory—and therefore, graph data structures—to persist data in a manner that is more faithful to real-world modeling.

Overview of Dynamically Configurable Data Block

Figure 3:
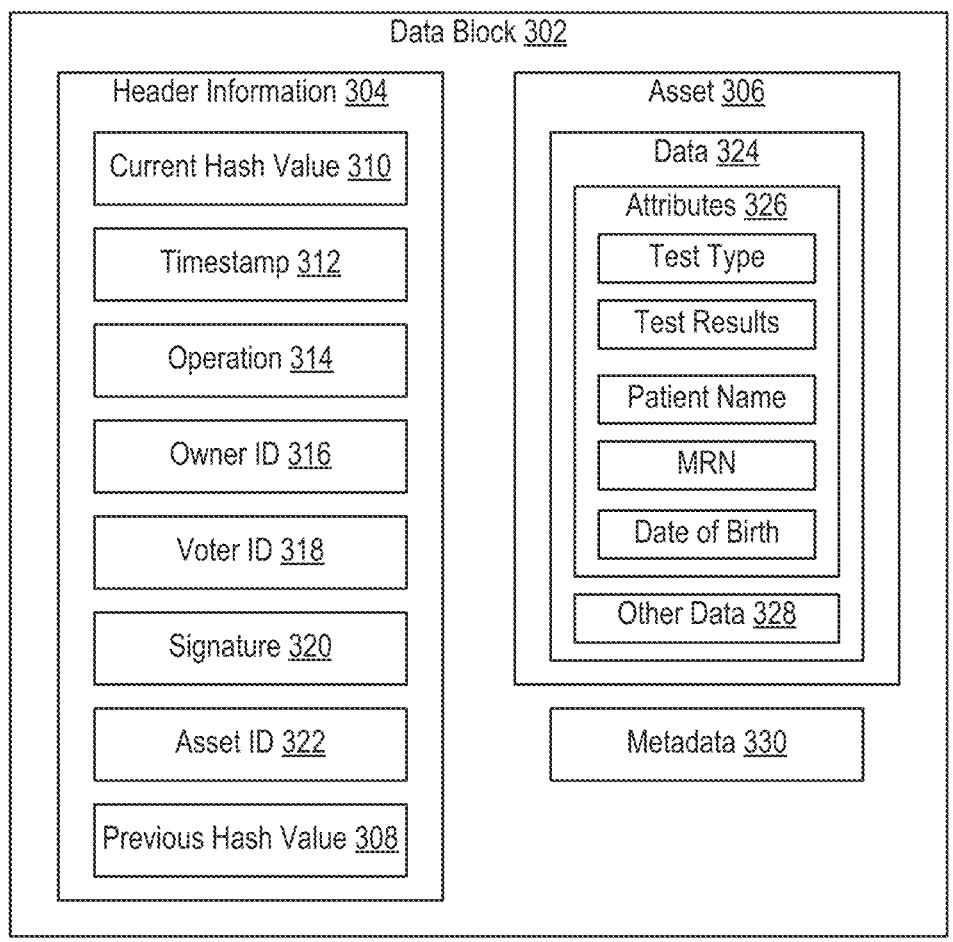
FIG. 3 illustrates an example of a data block that stores data as the asset.

FIG. 3 illustrates an example of a data block 302 that stores data 324 as the asset 306. The data block 302 is one type of block that can be stored in a blockchain (e.g., blockchain 100 of FIG. 1) of the computational architecture further described below. Thus, any of the blocks 102 in FIG. 1 may be a data block 302. In FIG. 3, the asset 306 stores data 324 in the form of attributes 326. At a high level, the attributes 326 may be representative of named variables with stored values that can be retrieved by name. In the embodiment shown in FIG. 3, the attributes 326 are listed by name: "test type," "test results," "patient name," "medical record number" or "MRN," and "date of birth." These attributes 326 are examples of PHI and PII; however, the attributes 326 could be any type of data as mentioned above. Thus, the attributes 326 need not necessarily be representative of PHI and PII. Accordingly, the asset 306 may store additional or alternative attributes 326 than those shown in FIG. 3. The attributes 326 represent one way in which the data 324 may be organized and stored in the asset 306. The asset 306 could store the data 324 in other ways without departing from the present disclosure.

Importantly, unlike other blockchain implementations that enforce fixed structure and fields for all data assets on the blockchain, each data block 302 on the blockchain may differ from preceding and subsequent blocks in terms of the specific attributes 326 and the named variables stored in the data block 302, such that one data block may store "test type," "test results," "patient name," "medical record number," and "date of birth," while another data block on the same blockchain may store "claim number," "amount," and "procedure code," for example. Each data block 302 may include a different number of fields within its asset 306, each field representing an attribute 326. Accordingly, due to the variability in number and structure of attributes 326 on each data block 302, each data block 302 may vary significantly from other data blocks 302 in terms of overall block size. Because each data block 302 acts as an independent and autonomous smart data object having its own security, structure, and ownership information engaged with the data, a single blockchain is able host a heterogenous set (or chain) of data blocks with different configurations, yet allow those blocks to interact under consent contracts as further discussed below.

While the computational architecture may be able to store large amounts of information in each block on the blockchain, it may be preferable to store some large objects (e.g., binary large objects and character large objects) off chain. The computational architecture may allow structured or unstructured data to be stored in an asset, but could also perform validation or conversion to adhere to a desired specification.

The variability afforded to the data blocks 302 allows the computational architecture to support diverse types of data on the same blockchain, which enables that blockchain to easily adapt to the addition of new data sources, types, and structures. When a novel data type is presented to that blockchain as a new data block 302, that blockchain does not need to reject the new data block 302, nor does that blockchain need to be completely restructured and redeployed to support the new data type. The new data type may be added to that blockchain, so long as the consensus protocol validates the new data block 302 to be appended to that blockchain.

For clarity in FIG. 3, the header information 304 is shown storing the previous hash value 308. Thus, when the header information 304 is hashed in its entirety, the previous hash value 308 is included. The header information 304 may also include a current hash value 310 that uniquely labels the data block 302. The header information 304 may also include a timestamp 312 that identifies the date or time when the data block 302 was created (e.g., added to the blockchain). The header information 304 may also include an operation 314 that identifies how the data block 302 is to be used by the blockchain. For example, the operation 314 may be a text string (e.g., "create") that indicates the nature of the data block 302 (e.g., that the data block 302 stores data 324). Other examples of operations are further discussed below.

The header information 304 may also include an owner identifier (ID) 316 that identifies one or more entities that own the asset 306, and thus control access to the asset 306. Examples of entities include individuals, companies, organizations, and the like. The owner ID 316 may be, for example, one or more publicly available address strings that uniquely identify the corresponding one or more entities that own the data block 302. Importantly, a data block may be owned by one or more entities, each entity bearing different types of ownership rights. Three examples of different types of ownership are described below in Table I.

TABLE I

Examples of different types of asset ownership.

| Type | Description |
| --- | --- |
| Owner | In the simplest concept, an owner has complete control over the asset. As such, an owner may be able to perform CRUD + T operations with respect to assets, as well as consent to sharing those assets. |
| Limited Owner | A limited owner may have complete control over how an asset is shared, but without writing, delete, or transfer privileges. As an example, in a use case involving laboratory results, patients may be permitted to read and share those results but may not have the authority to edit those results. |
| Multi-Owner | Also referred to as a "co-owner" or "equity owner" situation, In this situation, any one of the owners may have complete control over the asset, and therefore be permitted to perform CRUD + T operations and provide consent. |

The header information 304 may also include a voter identifier (ID) 318 that identifies the nodes in the distributed computing network that verified the data block 302. The voter ID 318 may be a publicly available address string that uniquely identifies the node.

The header information 304 may also include a signature 320 that is formed when an owner of the data block 302 cryptographically signs the current hash 310 with a private key (e.g., from a public-private key pair). The signature 320 may allow an entity to verify (i) the integrity of the asset 306 (e.g., by establishing that the asset 306 has not been altered since the data block 302 was added to the blockchain) and (ii) the owner(s) of the asset 306. More specifically, the entity can use the owner's public key to "unlock" the signature 320 and compare the result to a rehash of the data block 302 (e.g., a rehash of the header information 304 and asset 306). If these values agree, the integrity of the asset 306 and the owner can be deemed to be verified. However, if these values do not agree, then the source of the public key may not be the true owner of the data block 302, or the asset 306 may have been altered subsequent to its addition to the blockchain.

The header information 304 may also include an asset identifier (ID) 322 that identifies the asset 306. Since the asset 306 is essentially immutable as discussed above, any change to the asset 306 may be implemented by adding the changed asset to the blockchain as a new data block. Consider, for example, a first data block 302(*i*) that includes a first asset 306(*i*). The owner then changes the first asset 306(*i*) into a second asset 306(*j*) that is stored in a subsequent second data block 302(*j*). In such a situation, the first and second data blocks 302(*i*)-(*j*) can store the same asset ID 322, indicating that the second data block 302(*j*) is meant to replace the first data block 302(*i*). The first data block 302(*i*) may include an operation 314(*i*) that is a text string, "create," while the second data block 302(*j*) may include an operation 314(*j*) that is a text string, "update." Thus, the computational architecture can indicate that the second asset 306(*j*) is essentially a newer version of the first asset 306(*i*) using the asset ID 322. When retrieving the asset 306 from the blockchain, only the latest (i.e., most recent) version of the asset 306 may be returned. In this way, the computational architecture is able to store the state of a data asset together with the asset itself.

As shown in FIG. 3, the data block 302 may also include metadata 330. The metadata 330 may allow users to add additional information about the asset 306. For example, this information may relate to the original source (e.g., an Internet Protocol address for a computing device). Metadata 330 may not always be necessary, and thus may not be included in some embodiments. However, the metadata 330 provides flexibility that users can employ to provide further information about asset 306.

Overview of Consent Block

Figure 4A:
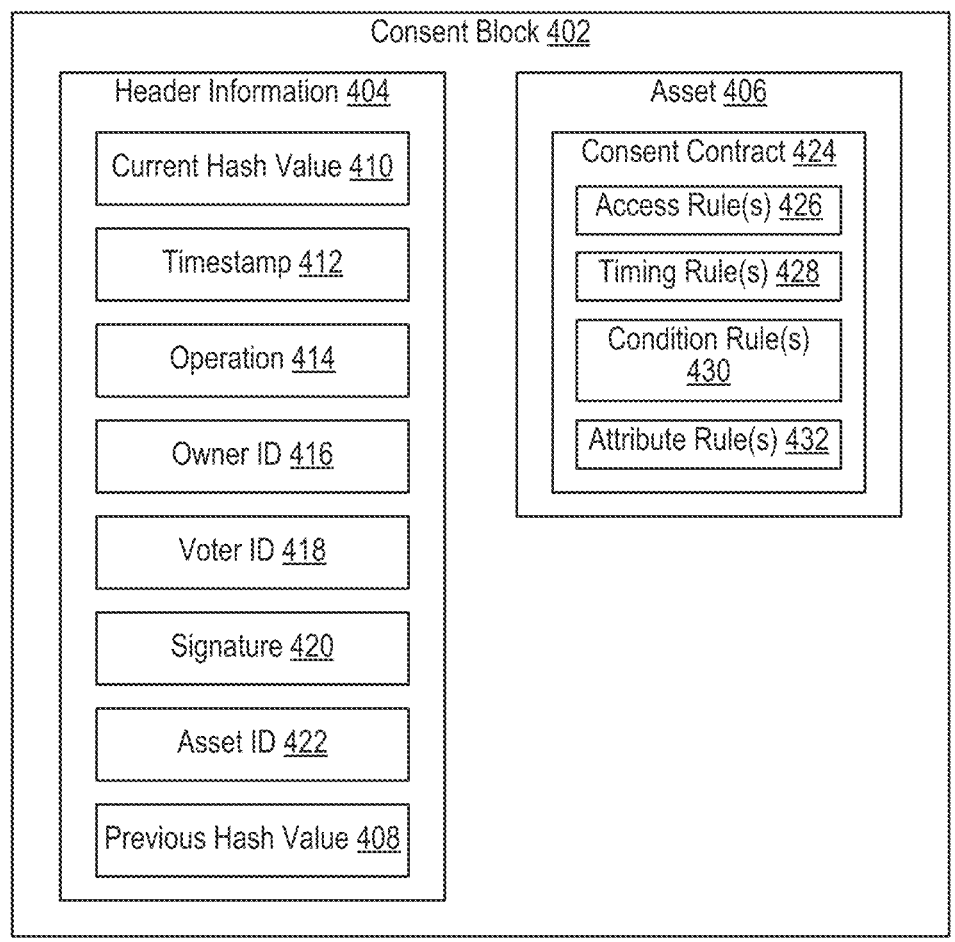
FIG. 4A illustrates an example of a consent block that is similar to the data block of FIG. 3, except that it stores a consent contract as its asset instead of data.

FIG. 4A illustrates an example of a consent block 402 (also referred to as a "smart contract block") that is similar to the data block 302 of FIG. 3, except that it stores a consent contract 424 as its asset 406 instead of data. However, the consent block 402 may still include header information 404, a previous hash value 408, and a current hash value 410 in addition to the asset 406 as shown in FIG. 4A. The consent block 402 is another type of block that can be stored in a blockchain (e.g., blockchain 100 of FIG. 1). Thus, any of the blocks 102 in FIG. 1 may be a consent block 402.

The current hash value 410, timestamp 412, operation 414, owner ID 416, voter ID 418, signature 420, and asset ID 422 of the consent block 402 may be substantially similar to the current hash value 310, timestamp 312, operation 314, owner ID 316, voter ID 318, signature 320, and asset ID 322 of the data block 302 shown in FIG. 3. As such, those elements are not described at length with reference to FIG. 4A.

The consent contract 424 is representative of a smart contract that allows its owner (e.g., as identified by owner ID 316, 416) to grant read-only access to the data stored in data blocks that are also owned by the same owner. Said another way, the owner of a data block can define which entity or entities are permitted to access the data stored in the data block 302 by creating a consent contract 424 that is stored in a consent block 402. The data block 302 and consent block 402 may be known to be owned by the same owner based on the respective owner IDs 316, 416. Access to the data can be granted to one or more entities whose owner IDs are different than that of the owner.

As shown in FIG. 4A, the consent contract 424 may include one or more access rules 426, one or more timing rules 428, one or more condition rules 430, one or more attribute rules 432, or any combination thereof. Each of these types of rules is discussed below. Note, however, that any combination of these types of rules could be applicable to a given consent contract.

The consent contract 424 may include access rule(s) 426 that determine which entity or entities are permitted to access the data stored in the data block 302. In one embodiment, the access rule(s) 426 may include one or more owner IDs that are different than owner ID 416. In another embodiment, the access rule(s) 426 may include one or more roles (e.g., 'researcher') that are associated with one or more owner IDs. In a third embodiment, the access rule(s) 426 may be unbounded, in which case access is granted to all owner IDs.

The consent contract 424 may include timing rule(s) 428 that determine when the consent is active. The timing rule(s) 428 may specify an expiration date such that access granted by the consent contract 424 ceases after the expiration date. Moreover, the timing rule(s) 428 may specify an expiration time such that the consent contract 424 ceases after the expiration time on the expiration date. The timing rule(s) 428 may also specify a future start state (and optional future start time) after which the consent contract 424 takes effect. When the timing rule(s) 428 include both start and expiration dates, the consent contract 424 will only be active during the timeframe bounded by the start and expiration dates.

The consent contract 424 may include condition rule(s) 430 that determine the criteria that must be present for the consent to take effect. As an example, within a data block 302 that is determined to be owned by the same owner as the consent block 402 based on the respective owner IDs, if an attribute 326 or other data 328 within data block 302 meets the criteria of the condition rule 430, then consent takes effect. A condition rule 430 may specify criteria applicable to a single attribute 326, multiple attributes 326, other data 328, or any combination thereof. By way of example, a condition rule 430 in a consent contract 424 may specify that if attribute 326, defined in this example as "test_type," is equal to "CBC," then consent shall be granted to the entity or entities identified in access rule 426 of the consent contract 424. Thereafter, if the entity identified in the access rule 426 of consent contract 424 performs a query for all data blocks containing test_type=CBC, then the consent contract 424 shall take effect and the entity or entities identified in access rule(s) 426 shall be granted access.

The consent contract 424 may include attribute rule(s) 432 that specify which attribute(s) 326 and/or other data 328 are accessible to the recipient(s) specified by the access rule(s) 426. As an example, an attribute rule 432 may specify that access is granted to a single attribute 326, multiple attributes 326, all attributes 326, other data 328, or any combination thereof. Thus, access may be permitted for some or all of the data within the data block 302.

An owner may create a consent contract 424 that grants read-only access to a single data attribute within a data block 302, all data stored on a single data block 302, data stored across multiple data blocks 302, or any other combination of data attributes 326 stored on blockchain(s) of the computational architecture, without departing from the scope of the invention.

Similar to the data block 302, the header information 404 of the consent block 402 may also include an asset ID 422 that identifies the asset 406, such asset 406 being comprised of the consent contract 424. Since the asset 406 is essentially immutable as discussed above, any change to the consent contract 424 may be implemented by adding the changed consent contract to the blockchain as a new consent block. Consider, for example, a first consent block 402(i) that includes a first consent contract 424(i). The owner then changes the first consent contract 424(i) into a second consent contract 424(j) that is stored in a subsequent second consent contract block 402(j). In such a situation, the first and second consent blocks 402(i)-(j) can store the same asset ID 422, indicating that the second consent block 402(j) is meant to replace the first consent block 402(i). The first consent block 402(i) may include an operation 414(i) that is a text string, "create," while the second consent block 402(j) may include an operation 414(j) that is a text string, "update." Thus, the computational architecture can indicate that the second consent contract 424(j) is essentially a newer version of the first consent contract 424(i) using the asset ID 422. When retrieving the consent contract 424 from the blockchain, only the latest (i.e., most recent) version of the consent contract 424 may be returned. In this way, the computational architecture is able to update consent contracts while maintaining a record of previous consents.

The consent contract 424 can also store executable instructions that add to, or modify, the selection criteria of a query that is executed on the blockchain. As an example, the blocks of the blockchain may be accessed, in response to a query, to identify all relevant consent contracts 424 that are stored in the blockchain. In this first pass through the blocks, only the consent blocks 402 may be accessed. That is, the data blocks (e.g., data block 302 of FIG. 3) and asset blocks may initially be ignored. The access rule(s) 426, timing rule(s) 428, condition rule(s) 430, and attribute rule(s) 432 from those consent contracts 424 can be combined with the selection criteria of the query to create augmented selection criteria. For example, the owner-specified access rule(s) may be joined (e.g., conjunctively or disjunctively) with the selection criteria to form the augmented selection criteria. The blocks on the blockchain can then be accessed a second time to create a result set of data blocks 302 that meet the augmented selection criteria. The asset 306 of each data block 302 included in the result set can then be accessed and retrieved.

Figure 4B:
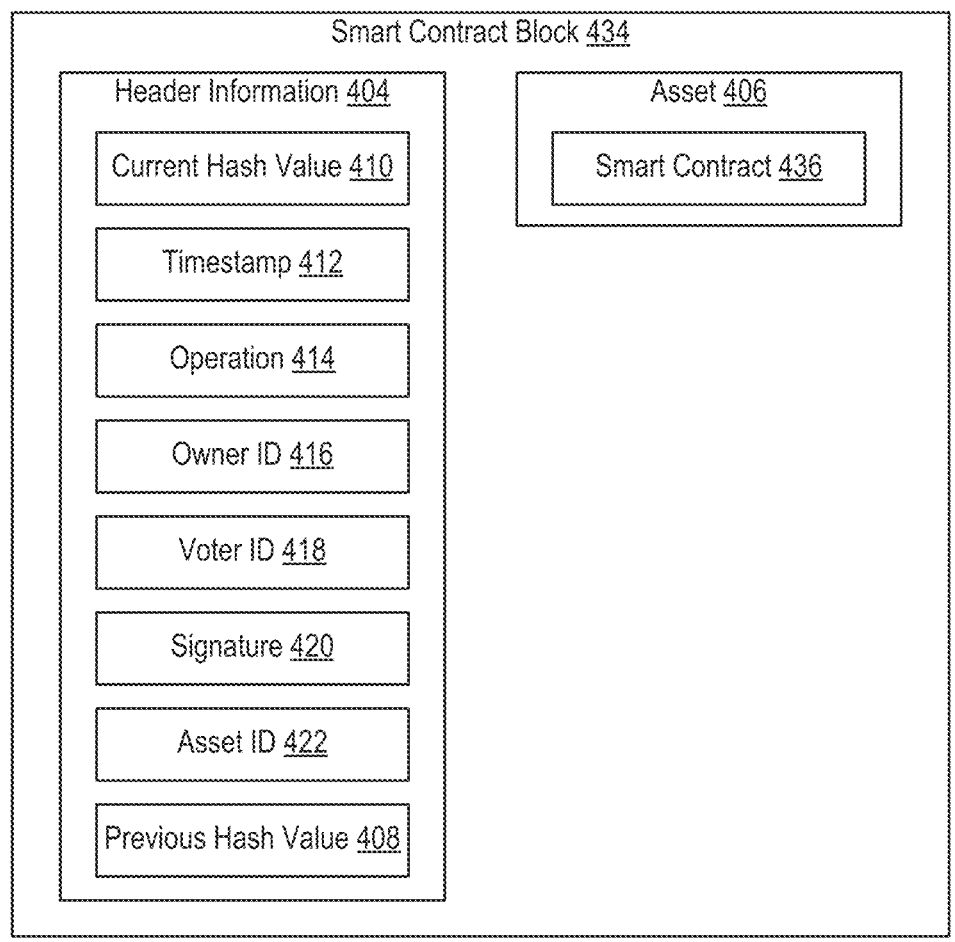
FIG. 4B illustrates an example of a smart contract block that is similar to the consent block of FIG. 4A, except that it stores a smart contract as its asset.

FIG. 4B illustrates an example of a smart contract block 434 that is similar to the consent block of FIG. 4A, and therefore its components are not described at length. However, the smart contract block 434 stores a smart contract 436 as its asset 406 rather than a consent contract.

Figure 5:
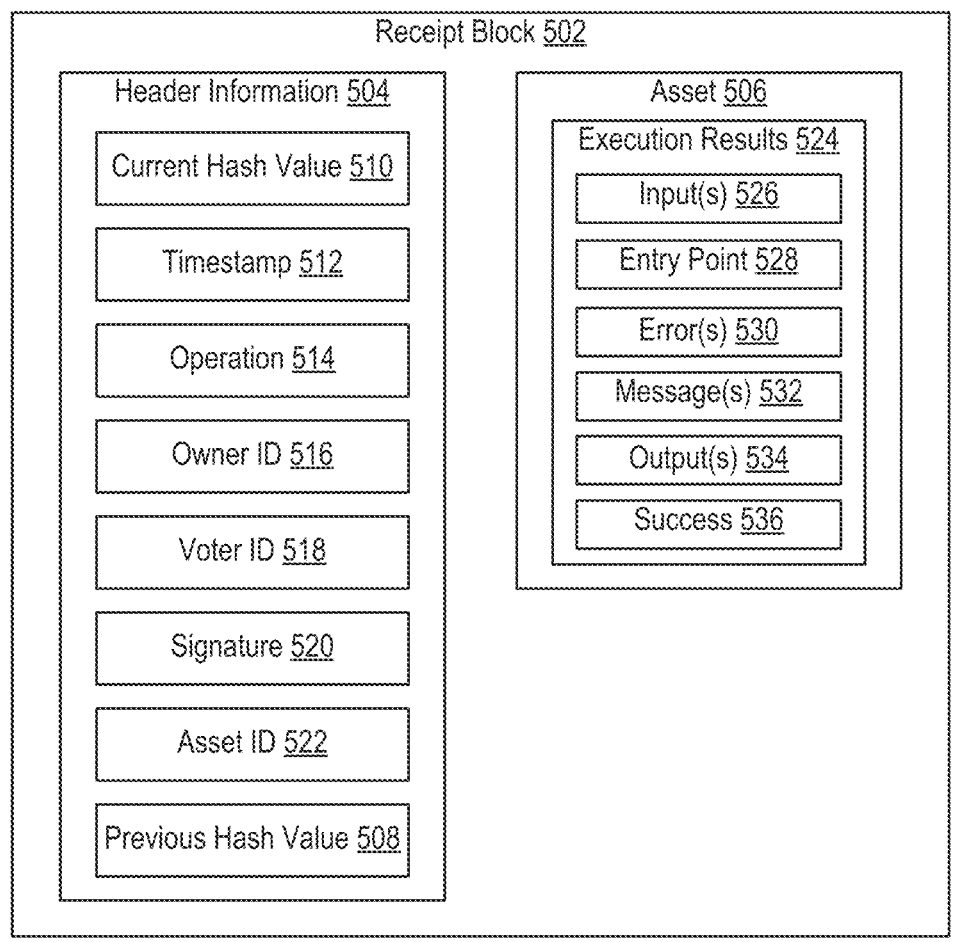
FIG. 5 illustrates an example of a receipt block that is similar to the data block of FIG. 3, except that it stores results of execution of the smart contract as its asset.

FIG. 5 illustrates an example of a receipt block 502 that is similar to the data block 302 of FIG. 3, except that it stores results 524 of execution of a consent contract (e.g., consent contract 424 of FIG. 4A) as its asset 506. The consent contract execution results 524 (or simply "execution results") could include or indicate, for example, the assets that were viewed via the consent contract, the numbered of altered assets from execution of the smart contract, etc. Each consent contract may generate a receipt block 502 whenever it is accessed for a query. Said another way, the receipt block 502 may occur for each smart contract (e.g., embodied in consent block 402 of FIG. 4A or smart contract block 434 of FIG. 4B) that is executed by the computational architecture. Thus, the receipt block 502 may serve as a record of when the blockchain (and, more specifically, its smart contracts) was queried. Note that the same receipt block may be used whether the smart contract is a consent contract or another type of smart contract.

As shown in FIG. 5, the receipt block 502 may include header information 504, a previous hash value 508, and a current hash value 510 (also called a "receipt hash value") in addition to the asset 506. The criteria may include the owner ID 516 of the entity performing the query, the assets and/or attributes requested by the selection criteria, and/or the augmented selection criteria as generated by the modification process discussed above. The execution results 524 may include the asset ID 322 and attributes 326 that are retrieved from the blockchain. The receipt block 502 is another type of block that can be stored in a blockchain (e.g., blockchain 100 of FIG. 1). Thus, any of the blocks 102 in FIG. 1 may be a receipt block 502.

The current hash value 510, timestamp 512, operation 514, owner ID 516, voter ID 518, signature 520, and asset ID 522 of the receipt block 502 may be substantially similar to the current hash value 310, timestamp 312, operation 314, owner ID 316, voter ID 318, signature 320, and asset ID 322 of the data block 302 shown in FIG. 3. As such, those elements are not described at length with reference to FIG. 5.

As shown in FIG. 5, the execution results 524 may include one or more inputs 526, an entry point 528, one or more errors 530, one or more messages 532, one or more outputs 534 (also called "responses"), an indicator of success 536, or any combination thereof. Note that any combination of these items could be included in the execution results 524 depending on, for example, the nature of the smart contract that is executed.

To reduce growth of the blockchain, each receipt block 502 may alternatively be stored in another blockchain that is separately managed. Thus, receipt blocks may be stored in a blockchain separate from the one that includes data blocks, consent blocks, smart contract blocks, and graph data blocks. Receipt blocks 502 can serve not only as a record of when the blockchain was queried, but also of which blocks were accessed. Thus, receipt blocks 502 may be useful in an audit to verify the integrity of the blockchain and to track and report data access events for compliance purposes.

Examples of Consent Contracts

FIGS. 6A-E include examples that show how a consent contract (e.g., consent contract 424 of FIG. 4A) can grant access to data in data blocks (e.g., data block 302 of FIG. 3). FIG. 6A depicts an example of a one-to-one consent contract 610 in which an owner of the one-to-one consent contract 610 grants access to a single entity. The owner can be identified by the owner ID of the corresponding consent block (e.g., consent block 402 of FIG. 4A). In the first line of the one-to-one consent contract 610, an address is populated following the keyword "consents." The address is representative of a public identifier that identifies the entity receiving the access. This may be representative of an example of an access rule (e.g., access rule 426 of FIG. 4A). In the second line of the one-to-one consent contract 610, the phrase "for chain_name" indicates that the one-to-one consent contract 610 only applies to the blockchain with the identifier chain_name.

In the third line of the one-to-one consent contract 610, the keyword "when" is followed by a logical statement that must be satisfied for access to be granted. In the examples depicted in FIGS. 6A-C, the logical statement is true when the asset ID of a data block equals the fixed value 15131. Accordingly, this one-to-one consent contract 610 will only grant access to the data in a data block having (i) the fixed value as its asset ID and (ii) the same owner (e.g., as determined from owner ID) as the one-to-one consent contract 610. The logical statement following the keyword "when" may include more than one fixed value for the asset ID (e.g., separated by commas, semi-colons, or spaces). In this case, the logical statement may be true when a data block stores any one of these fixed values for its asset ID. Alternatively, the logical statement may include wildcard symbols (e.g., *), for example, to indicate that access should be granted to all of the owner's data, regardless of the asset ID. This may be representative of an example of a condition rule (e.g., condition rule 430 of FIG. 4A).

In the examples depicted in FIGS. 6D-E, the logical statement specifies one or more types of assets. The consent contract 640 of FIG. 6D grants access when the attribute of the asset equals 'CBC,' while the consent contract 650 of FIG. 6E grants access when one attribute (test_type) of an asset equals 'CBC' and another attribute (location_id) equals 42. Similarly, the one-to-one consent contract 610 could include the statement "when asset.test_type=attribute_value." In this case, when the data in a data block includes an attribute named "test_type," the value store therein can be checked to see if it equals attribute_value. If so, access to the data in the data block may be granted. If not—or if there is no attribute named "test_type"—then access to the data block may not be granted. The one-to-one consent contract 610 may grant access to all of these data blocks without regard to the asset ID. Alternatively, the logical statement may combine requirements (e.g., for test_type and location_id) to limit access to a subset of the data blocks in which the attribute named "test_type" stores the value attribute_value. This may be representative of another example of a condition rule (e.g., condition rule 432 of FIG. 4A).

In the fourth line of the one-to-one consent contract 610, the keyword "until" is followed by a date that specifies when the one-to-one consent contract 610 expires. The specified data or time may be representative of an example of a timing rule (e.g., timing rule 428 of FIG. 4A). In the fifth line of the one-to-one consent contract 610, the keyword "only" is followed by a list of attribute names. Access may only be granted to an attribute whose name matches one of those listed (i.e., attr3, attr4, or attr5 in the example of FIG. 6A). This may be representative of an example of an attribute rule (e.g., attribute rule 432 of FIG. 4A).

FIG. 6B depicts an example of a one-to-many consent contract 620 that is similar to the one-to-one consent contract 610 of FIG. 6A, except that it grants access to more than one entity. In this case, two entities are identified by two addresses that appear after the keyword "consents." However, the one-to-many consent contract 620 may be expanded to grant access to more than two entities by listing additional addresses after the keyword "consents."

FIG. 6C, meanwhile, depicts an example of a one-to-type consent contract 630 that is similar to the one-to-one consent contract 610 of FIG. 6A, except that it grants access to an entity type rather than a specific entity associated with a specific address. In FIG. 6C, the entity type is "researcher." An entity that accesses the blockchain may be labeled in accordance with a predefined schema that includes one or more predetermined entity defined. When an entity that is labeled as a "researcher" attempts to access a data block governed by the one-to-type consent contract 630, the computational architecture may permit access. However, if the entity is not labeled as a "researcher" (e.g., is instead labeled as a "clinic," "practitioner," or "insurer"), the one-to-type consent contract 630 may not grant access.

Entities may be associated with more than one entity type. For example, a healthcare professional may be labeled as a "practitioner" and "researcher," As another example, a research hospital may be labeled as a "clinic" and "research institution." Similar to the one-to-many consent contract 620 of FIG. 6B, multiple entity types may be granted access using the one-to-type consent contract 630 (e.g., by listing more than one entity type after the keyword). Moreover, one or more addresses may be listed with the entity type(s). In such a scenario, access may be granted to specific entities associated with those addresses in addition to those entities associated with the entity type(s).

Example Computational Architectures for Creating and Recording Blocks

Figure 7:
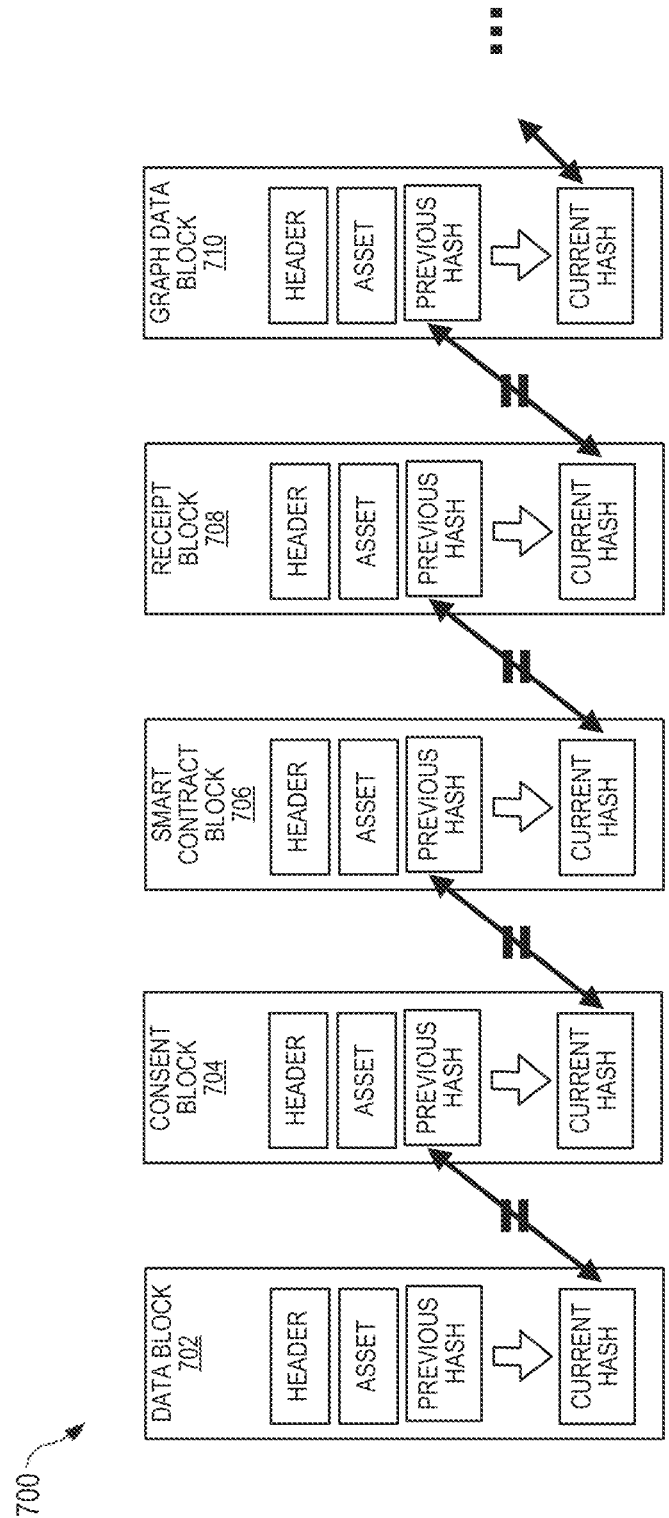
FIG. 7 illustrates how different types of data blocks, each with different fields, structures, owners, and block sizes, may be stored together on a blockchain with each other and with consent contracts of different types.

FIG. 7 illustrates how different types of blocks, each with different fields, structures, owners, and block sizes, may be stored together on a blockchain 700 with each other. As shown in FIG. 7, the blockchain 700 may include data blocks 702, consent blocks 704, smart contract blocks 706, receipt blocks 708, or graph data blocks 710 comparable to those described herein with reference to FIGS. 3, 4A, 4B, 5, and 10, respectively. For the purpose of illustration, the blockchain 700 includes a single block of each of the aforementioned types. However, those skilled in the art will recognize that the blockchain 700 could include any number of each block type. Generally, the blockchain 700 will include more data blocks 702 and graph data blocks 710 than consent blocks 704, smart contract blocks 706, or receipt blocks 708, but the ratio of block types will depend on the intended application of the data stored therein. The blockchain 700 may be generally comparable in its operation to blockchain 100 of FIG. 1. Owners may be able to readily add consent contracts to the blockchain 700 in corresponding consent blocks 704, thereby giving the owner the flexibility to determine who can access the data blocks 702 or graph data blocks 710 belonging to the owner, which parts of the assets can be accessed, and under what conditions those assets can be accessed. As mentioned above, each consent block 704 may include an asset ID with which the owner can update the corresponding consent contract. For example, the owners of a given consent block may add, to the blockchain, a new consent block with the same asset ID but different access rules or timing rules. In such a situation, the updated rules may supersede (i.e., take precedence over) the original rules in the given consent block, thereby allowing the owner to revise the original rules at any time—even after the given consent block has been added to the blockchain. When the blocks of the blockchain are sequentially accessed to identify all consent contracts, only the most recent consent contract with a particular asset ID may be used. Said another way, all prior consent contracts with the same asset ID may be ignored, as the corresponding rules have been superseded. This only applies when an existing consent contract is edited; however, multiple consent contracts could be "alive" for the same data block at a given point in time.

The nature of consent contracts also allows an owner to create several consent contracts that work together to determine the access to be granted to one or more entities. Thus, the owner may not be limited to issuing a single consent contract for a single entity. Rather, the owner can create multiple consent contracts, each stored in a corresponding consent block with a different asset ID and containing access rules for a single entity. If the asset IDs are different, access granted to the entity may be governed by all of the rules in the consent contract(s) that identify the entity. Thus, rules may be complementary in some situations (and thus may not supersede one another). In embodiments where the rules are complementary, the rules (e.g., from multiple consent contracts) may be combined to determine the access to grant to the entity.

Figure 8:
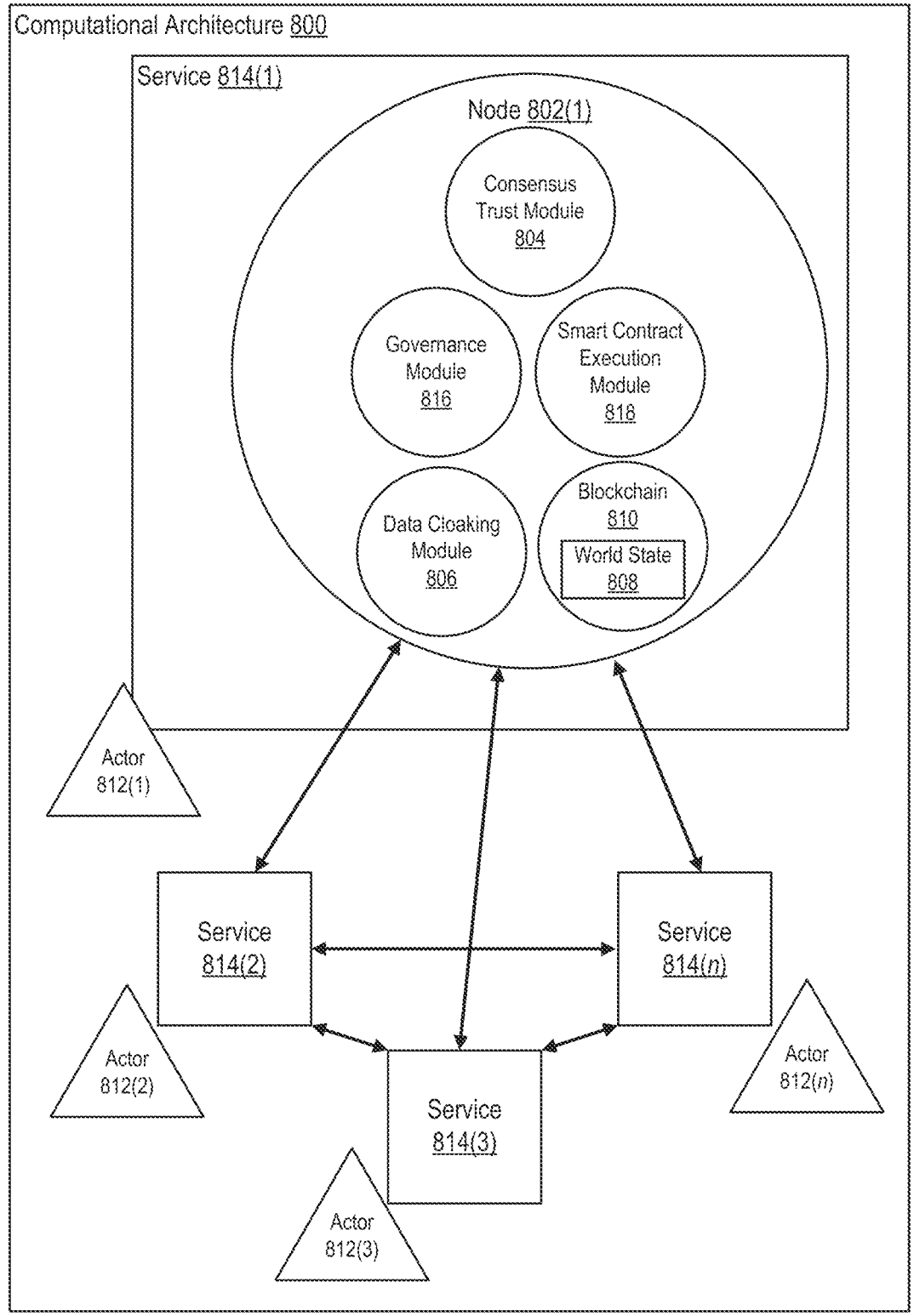
FIG. 8 includes a high-level illustration of a computational architecture with which embodiments can be implemented.

FIG. 8 includes a high-level illustration of a computational architecture 800 with which embodiments can be implemented. The computational architecture (also referred to as a "data storage platform," "data storage platform," or simply "platform") may be located, for example, on one or more computing devices that are accessible via a network (e.g., the Internet). For example, the computational architecture 800 may be hosted—partially or fully—on a private- or public-cloud architecture.

The computational architecture includes a plurality of interconnected nodes 802 that communicate with each other via the network. Each node may be representative of a computing device that includes a processor, associated memory, and one or more interfaces for communication. Each node 802 may be responsible for providing a service 814 to an actor 812. These services 814 may process, store, or otherwise handle data received from the actors 812. For example, these services 814 may make data in the world state 808 available to the actors 812.

Each node 802 of the computational architecture 800 may have software installed thereon. This software may be comprised of executable instructions in the memory that, when executed by the processor, control the node 802 to implement the functionalities described herein. Specifically, each node 802 may include a consensus trust module 804, a data cloaking module 806, and a world state 808 that represents one or more blockchains (e.g., created and maintained as discussed above with reference to FIG. 1), each blockchain being comprised of data blocks (e.g., similar to data block 302 of FIG. 3), consent blocks (e.g., similar to consent block 402 of FIG. 4A), and/or receipt blocks (e.g., similar to receipt block 502 of FIG. 5). The world state 808 also represents the permanent, persistent store of information committed to a blockchain 810. The consensus trust module 804 may provide the basis for managing trust across all components of the computational architecture 800 to ensure validity of the blockchain 810. Trust may be managed on a peer-to-peer (P2P) basis, such that the nodes 802 collectively manage trust. The nodes 802 can be connected in P2P manner using, for example, a leaderless gossip-based protocol. In such embodiments, communication for the consensus algorithm can occur via the Transmission Control Protocol/Internet Protocol ("TCP/IP") communication protocol or User Datagram Protocol ("UDP") communication protocol. Generally, the computational architecture 800 does not require a central trust management node. Instead, the nodes 802 may work concurrently and in competition with one another to validate access to the world state 808. Meanwhile, the world state 808 may be used to provide a proof of derivation for analytics purposes since, as mentioned above, the world state 808 represents the actual information committed to the blockchain 810.

The data cloaking module 806 may increase the security of data stored in the world state 808 by breaking the data into shards. Each shard may be placed in a secure ciphered (e.g., encrypted) container and then randomly distributed across the data store(s). In some embodiments, these secure ciphered containers are then periodically (e.g., hourly, daily, weekly) moved between the data store(s). Thus, the nodes 802 may cooperate to protect sensitive information while providing on-the-fly access to the data.

The world state 808, which represents the blockchain(s) 810, can be distributed across the nodes 802 to provide a secure record of blocks that cannot be altered. Since the world state 808 can be distributed across some or all of the nodes 802 on a network, the consensus trust module 804 in each node 802 will be aware of, and thus may validate, each transaction, thereby increasing the security of access to data in the data store(s). Thus, the world state 808 may be distributed across all notes on a network, or the world state 808 may be distributed across a subset of nodes on the network that is representative of a subnetwork. In this manner, the computational architecture may restrict distribution of world state 808, and the blockchain(s) 810 represented therein, to specific subnetworks based on a variety of requirements, including geographic location of the subnetwork nodes, attributes of the actor that is serviced by a node, or other requirements. This allows the computational architecture 800 to support policies and regulatory requirements that regulate the physical location of data.

The governance module 816 may be responsible for implementing consent contracts (e.g., consent contract 424 of FIG. 4A) that are included in consent blocks (e.g., consent block 402 of FIG. 4A) committed to the blockchain 810. Moreover, the governance module 816 may be responsible for supporting the data governance for owners and limited owners of blocks (e.g., data block 302 of FIG. 3 and graph data block 1002 of FIG. 10).

The smart contract execution module 818 may be responsible for implementing smart contracts (e.g., smart contract 436 of FIG. 4B) that are included in smart contract blocks (e.g., smart contract block 434 of FIG. 4B) committed to the blockchain 810.

Figure 9:
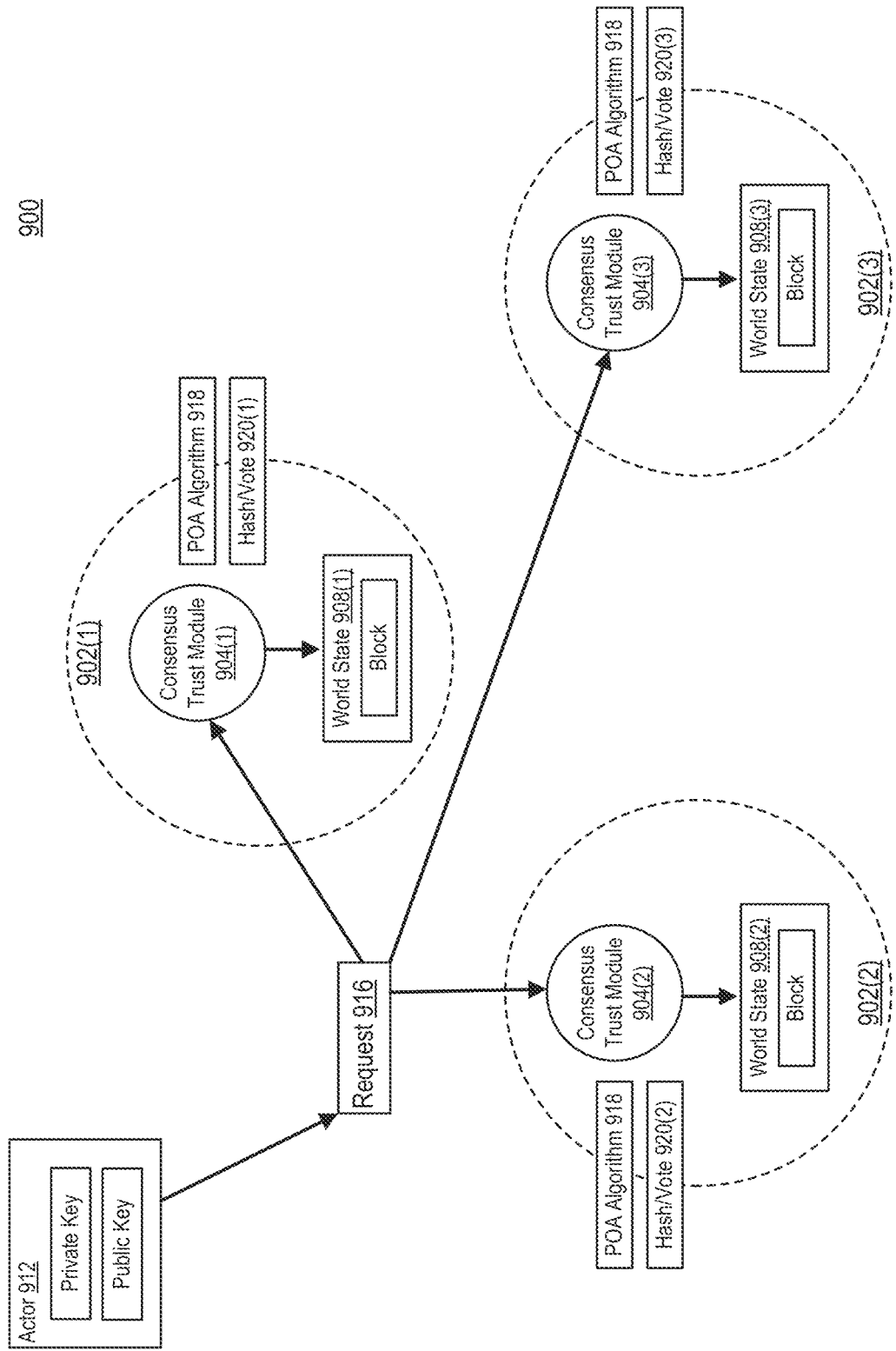
FIG. 9 illustrates how the consensus trust module of each network node is able to implement trust across the computational architecture in a distributed manner.

FIG. 9 illustrates how the consensus trust module 904 of each node is able to implement trust across the computational architecture 900 in a distributed manner. To store or access data in the computational architecture 900, an actor 912 can send a request 916 to any node 902. In the event that the request 916 involves data asset modification (e.g., create, update, delete, transfer), the receiving node verifies the action and then requests a plurality of votes from the other nodes in accordance with a consensus protocol. Consensus may be done across all nodes in the network, or consensus may be done across all nodes in a subnetwork of the network. Here, each node 902 is configured to implement an POA algorithm 918. Within each node 902, the consensus trust module 904 can use the POA algorithm 918 to determine a hash value 920 that defines the integrity of the data and integrity of other voters' calculated hash values. At a high level, each hash value is representative of a vote regarding whether the request 916 should be validated. Since each voter (e.g., nodes 902) is trusted and has a stake in maintaining the validity of the data on the computational architecture 900 for the collective good, it can vote on the validity of the data and hash value. In the event that the request 916 involves data asset access (e.g., query or read), the receiving node can fulfill the request on its own since all nodes in a subnetwork—but not the network as a whole—may have a complete copy of the world state 708.

The data included in the request 916 can then be updated with the hash value 920 and "pushed" to other nodes 902 that vote on the validity of the data until a majority of the network is reached. Accordingly, the POA algorithm 918 and hash values 920 may function as a check on the integrity of the data included in the request 916, as well as ensure that a proper owner of the data is identified. Assume, for example, that the actor 912 sends the request 916 to node 902(2), which then distributes the request 916 to nodes 902(1) and 902(3). Concurrently and independently within each node 902, the consensus trust module 904 can use the POA algorithm 918 to determine the corresponding hash value 920 (e.g., via a one-way hash function) based on the request 916. The consensus trust module 904 can then create and add a block corresponding to the hash value 920 to its world state 908 after a majority is reached, and this copy of the world state 908 can be automatically distributed to all other nodes 902 in the computational architecture 900.

Such an approach ensures that no single node 902 determines the trust of the request 916, and therefore the integrity of the computational architecture 900 has no single point of failure. As long as an attacker does not control more than half of the nodes 902, security of the computational architecture 900 will be preserved. The actor 912 may be granted access to data within the computational architecture 900 (e.g., within the world state 808 of FIG. 8) only when a majority of the consensus trust modules 904 agree. Said another way, only when a consensus of trust has been established for the actor 912 will the request 916 be acted upon by the data cloaking module (e.g., data cloaking module 806 of FIG. 8).

Figure 10:
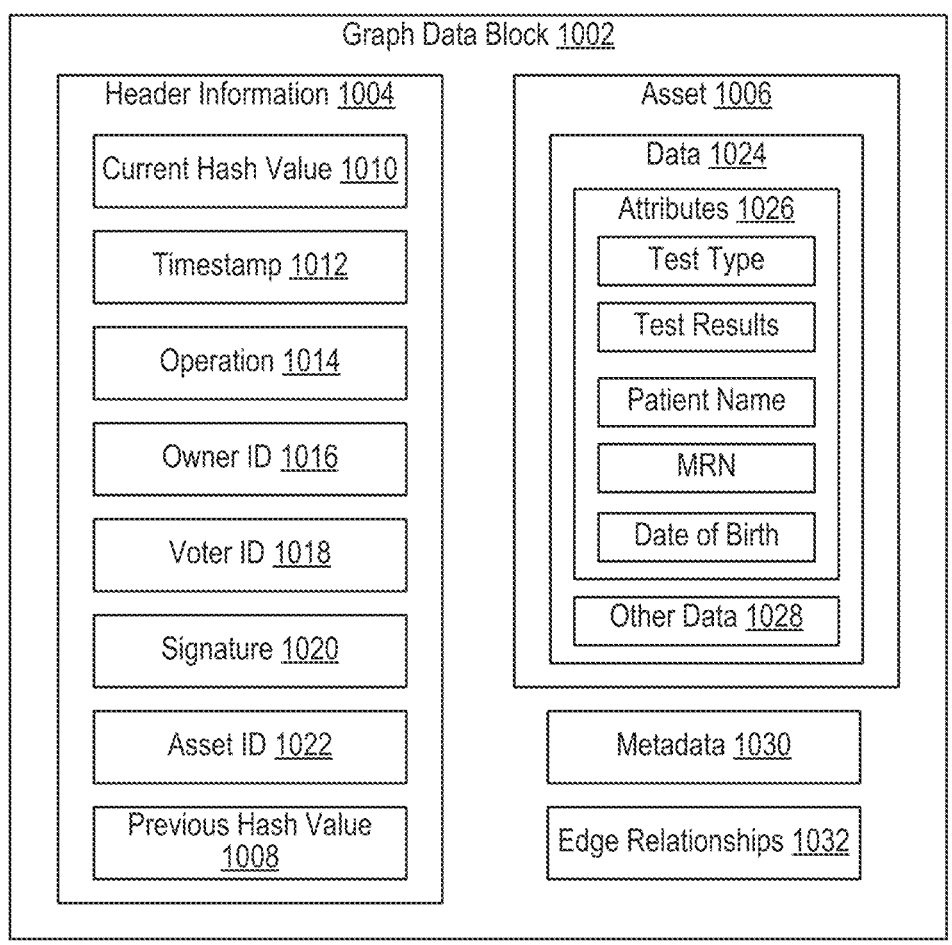
FIG. 10 includes a high-level illustration of a smart data object that shows how its data block may be comparable to the data block of FIG. 3 with the addition of metadata and edge relationships.

FIG. 10 illustrates a graph data block 1002 that may be comparable to the data block 302 of FIG. 3 with the addition of metadata 1030 and edge relationships 1032. As with the data block 302, the graph data block 1002 is treated as an autonomous unit of information—a "smart data object." The edge relationships 1032 define the explicit relationships between the asset 1006 and other asset(s) 1006 on other graph data block(s) 1002. This allows the asset 1006 in the graph data block 1002 to incorporate context into the smart data object model, and it allows the asset 1006 to be visualized in a graph model visualization, as described below.

The metadata 1030 may allow users to add additional information about the asset 1006. For example, this information may relate to the original source (e.g., an Internet Protocol address for a computing device). Metadata 1030 may not always be necessary, and thus may not be included in some embodiments. However, the metadata 1030 provides flexibility that users can employ to provide further information about asset 1006.

The current hash value 1010, timestamp 1012, operation 1014, owner ID 1016, voter ID 1018, signature 1020, and asset ID 1022 of the graph data block 1002 may be substantially similar to the current hash value 310, timestamp 312, operation 314, owner ID 316, voter ID 318, signature 320, and asset ID 322 of the data block 302 shown in FIG. 3. As such, those elements are not described at length with reference to FIG. 10.

Figure 11:
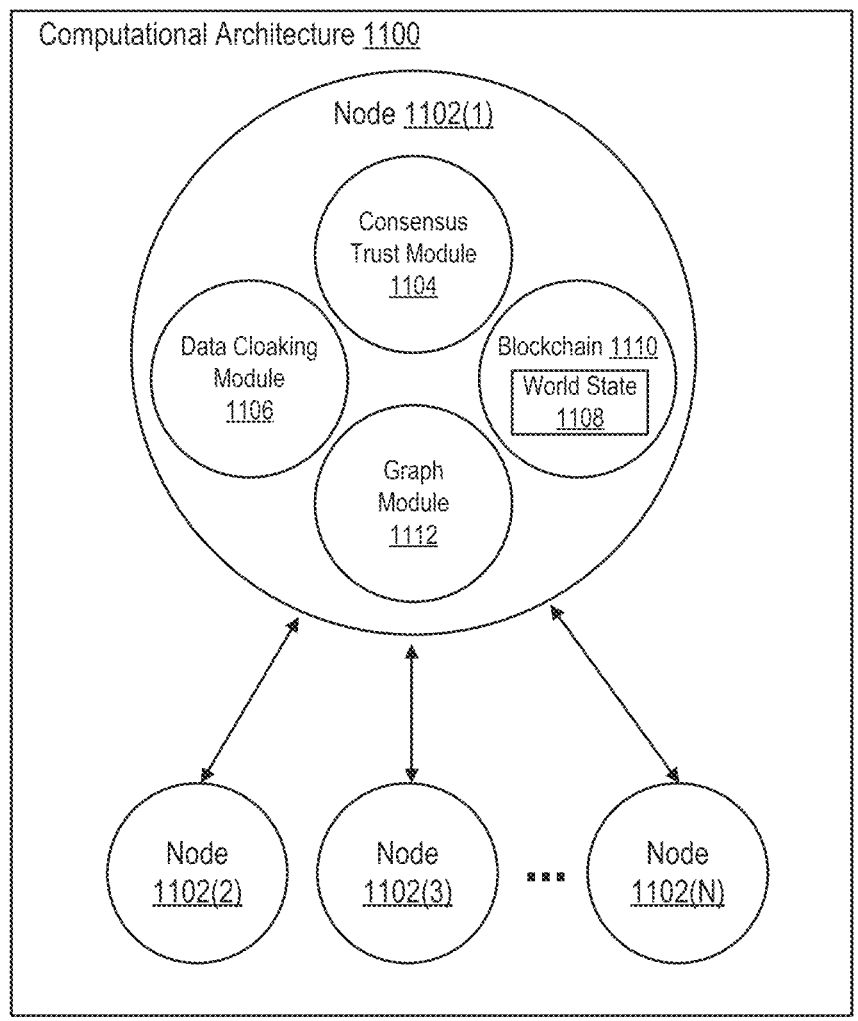
FIG. 11 includes a high-level illustration of a computational architecture that includes a graph modeling module in addition to a consensus trust module, data cloaking module, and blockchain on which the world state is stored.

FIG. 11 includes a high-level illustration of a computational architecture 1100 that may be comparable to the computational architecture 800 of FIG. 8, with the addition of a graph modeling module 1112 (or simply "graph module"). The consensus trust module 1104, data cloaking module 1106, and world state 1108 may be substantially similar to the consensus trust module 804, data cloaking module 806, and world state 808 shown in FIG. 8. As such, those elements are not described at length with reference to FIG. 11. Note also that while not shown in FIG. 11, the node 1102 may also include a governance module (e.g., similar to governance module 816 of FIG. 8) and smart contract execution module (e.g., similar to smart contract execution module 818 of FIG. 8). As shown in FIG. 11, the consensus trust module 1104, data cloaking module 1106, world state 1108, and graph module 1112 can be hosted on a node 1102. As mentioned above, these elements will normally be hosted on each node that is included in the computational architecture 1100. However, in some embodiments, the nodes of the computational architecture 1100 may simply be accessible to the graph module 1112. Thus, the graph module 1112 may not need to be instantiated on each node of the computational architecture 1100.

The graph module 1112 has deep roots into the actual graph mechanisms within the computational architecture 1100. Generally, the application programing interfaces ("APIs") executed by the graph module 1112 at runtime deal with data agnostically, such that data can be validated and managed per blockchain. Accordingly, the APIs may be generally applicable (e.g., for saving an asset to a chain) rather than specific to certain use cases (e.g., for saving a given asset to a given chain).

The graph module 1112 may be responsible for creating a series of blockchains on behalf of an administrator. Within a blockchain, each block (e.g., data block 302, consent block 402, or receipt block 502 of FIGS. 3, 4, and 5, respectively) may be viewed as a graph node in the graph module 1112. Any block may be the subject of the graph model produced by the graph module 1112. The "core" block may be associated with an entity. This entity may also be referred to as the "subject" of the graph model. Examples of entities include people (e.g., patients and healthcare professionals), places (e.g., healthcare facilities), organizations (e.g., healthcare systems and insurers), and things (e.g., Internet-of-Things devices and sensors). Other blockchains or blocks, through the edge relationships 1032 of the graph data block 1002, can provide context regarding the entity and contribute to the graph model as related graph nodes. As an example, if the entity is a healthcare professional, then other graph data blocks 1002 may include information regarding credentials, tests performed, vaccinations received, and the like. These relationships may be predefined as a starting point for creating the graph model. However, as mentioned above, additional relationships could be created based on, for example, implied relationships that are learned by ML or AI algorithms.

Further information on the computational architecture can be found in US Publication No. 2020/0389309 that is titled "Systems and Methods for Accessing Digital Assets in a Blockchain Using Owner Consent Contracts," US Publication No. 2022/0058282 that is titled "Systems and Methods for Accessing Digital Assets in a Blockchain Using Global Consent Contracts," and US Publication No. 2019/0012466 that is titled "Secure Adaptive Storage Platform," each of which is incorporated by reference herein in its entirety.

Exemplary Embodiments of Computational Architecture

Several embodiments of the computational architecture 1100 are envisioned, each with its own capabilities in processing, documenting, and managing on-chain data.

A. Computational Architecture with Graph Databases

In a first embodiment, the computational architecture 1100 includes a plurality of nodes 1102 that collectively implement a blockchain 1110. A plurality of graph databases can be distributed amongst the plurality of nodes 1102, such that each of the plurality of graph databases is associated with a corresponding one of the plurality of nodes 1102. Each of the plurality of graph databases may include a persistent store of data that is committed to the blockchain 1110, for example, in the form of the world state 1108. Each of the plurality of nodes 1102 can include a processor and associated memory with instructions stored therein that, when executed by the processor, implement a consensus trust module 1104 and graph module 1112.

Upon receiving input indicative of a request to store first data in the corresponding graph database, the consensus trust module 1104 can generate a hash value that is representative of integrity of the first data and then distribute the first data, updated with the hash value, to the other nodes of the plurality of nodes 1102. This first block can then go through consensus, as described above with confirmation by a majority of the plurality of nodes. Note that the plurality of nodes 1102 may be representative of all nodes managed by the computational architecture 1100 or associated with the blockchain 1110, or the plurality of nodes 1102 may be a subset of the nodes managed by the computational architecture 1100 or associated with the blockchain 1110. Thus, blocks may be distributed across subnetworks of nodes rather than the entire network of nodes that implements the blockchain 1110.

Upon confirming that the hash value has also been generated by a majority of the plurality of nodes, the consensus trust module 1104 can create a first block that includes the first data. Note that the term "create," as used in this context, refers to populating the first data into a data structure (e.g., that is similar to graph data block 1002 of FIG. 2). Thus, the consensus trust module 1104 may not immediately commit the first block to the blockchain 1110; instead, the first block may not be committed to the blockchain 1110 until relationship information has been populated therein, as necessary, by the graph module 1112.

To establish whether a relationship exists between the first data and data on the blockchain 1110, the graph module 1112 can employ a trained algorithm. Specifically, the graph module 1112 can apply a trained algorithm to autonomously learn a relationship between the first data in the first block and second data in a second block that is part of the blockchain 1110. Thereafter, the graph module 1112 can populate information regarding the relationship into the first block, so as to document the relationship with the second block, and then add the first block onto the blockchain for distribution to the plurality of nodes 1102 and storage in the plurality of graph databases.

In some embodiments, the graph module 1112 is further able to model the relationship by representing the first and second blocks as graph nodes in a graph structure. In the graph structure, the corresponding first and second graph nodes may be interconnected with an edge to indicate the relationship. Moreover, the graph module 1112 may cause display of a visualization that is representative of the graph structure. As discussed above, each node in the graph structure may be representative of a separate smart data object, and each smart data object may be committed to the blockchain 1110. However, the graph structure may not be committed to the blockchain 1110 in its entirety. Instead, the individual "building blocks" of the graph structure can be committed to the blockchain 1110 as graph data blocks.

Upon receiving input indicative of a query, the graph module 1112 may employ another algorithm to search the corresponding graph database to determine whether a matching block that satisfies the query exists. Because the graph database exists on each of the plurality of nodes 1102, consensus may not be necessary for a search operation. Instead, the graph module 1112 may simply apply this other algorithm to the corresponding graph data to identify matching blocks, if any. This other algorithm may be a depth-first algorithm or breadth-first algorithm.

B. Computational Architecture with Configurable Blocks

In a second embodiment, the computational architecture 1100 includes (i) a plurality of nodes 1102 that collectively implement a blockchain 1110 and (ii) a plurality of graph databases can be distributed amongst the plurality of nodes 1102, such that each of the plurality of graph databases is associated with a corresponding one of the plurality of nodes 1102. Each of the plurality of graph databases may include a persistent store of data that is committed to the blockchain 1110, for example, in the form of the world state 1108. Each of the plurality of nodes 1102 can include a processor and associated memory with instructions stored therein that, when executed by the processor, implement a consensus trust module 1104 and graph module 1112.

Upon receiving input indicative of a request to store first data in the corresponding graph database, the consensus trust module 1104 can generate a hash value that is representative of integrity of the first data and then distribute the first data, updated with the hash value, to the other nodes of the plurality of nodes 1102. Similar to the aforementioned first example, this first block can then go through consensus. Upon confirming that the hash value has also been generated by a majority of the plurality of nodes, the consensus trust module 1104 can dynamically configure a first block to have an appropriate field count, an appropriate field size, and/or an appropriate field schema to accommodate the first data and then populate the first data in the first block. Thus, the consensus trust module 1104 can tailor the first block for the first data. Generally, the field count is not a limiting factor, though a given block may include 5-20 fields. Generally, a given block will be between 256-512 bytes at the "small end" and 10 megabytes at the "large end," though blocks could be smaller or larger as necessary. For computational efficiency reasons, the optimal maximum block size may be 75 kilobytes. Meanwhile, field schemas are normally predefined to accommodate different types of data. For example, a given block could be configurable to have text fields, numerical fields, unstructured fields, or a combination thereof. The appropriate field schema can be identified by the consensus trust module 1104 based on an analysis of the first data. The first data may be populated into the first block in its "raw" form, or the first data may be populated into the first block in its "processed" form. As a specific example, the first data may be stored in the first block as a JavaScript Object Notation (JSON) document.

Thereafter, the graph module 1112 can determine that a relationship exists between the first data in the first block and second data in a second block that is part of the blockchain 1110. This could be accomplished using a data structure with rules codified therein—which may be called a "dictionary" as mentioned above—or a trained algorithm. The graph module 1112 can populate information regarding the relationship into the first block, so as to document the relationship with the second block, and then add the first block onto the blockchain for distribution to the plurality of nodes 1102 and storage in the plurality of graph databases.

C. Computational Architecture with Sidechains

In a third embodiment, the computational architecture 1100 includes (i) a plurality of nodes 1102 that collectively implement a blockchain 1110 and (ii) a plurality of graph databases can be distributed amongst the plurality of nodes 1102, such that each of the plurality of graph databases is associated with a corresponding one of the plurality of nodes 1102. Each of the plurality of graph databases may include a persistent store of data that is committed to the blockchain 1110, for example, in the form of the world state 1108. Each of the plurality of nodes 1102 can include a processor and associated memory with instructions stored therein that, when executed by the processor, implement a consensus trust module 1104 and graph module 1112.

Upon receiving input indicative of a request to store data in the corresponding graph database, the consensus trust module 1104 can generate a hash value that is representative of integrity of the data and then distribute the data, updated with the hash value, to the other nodes of the plurality of nodes 1102. Similar to the aforementioned first example, this block can then go through consensus. Upon confirming that the hash value has also been generated by a majority of the plurality of nodes, the consensus trust module 1104 can create a block that includes (i) the data and (ii) an identifier that uniquely identifies the data. Examples of identifiers are shown in FIG. 3 as the asset ID 322 and FIG. 10 as the asset ID 1022.

Thereafter, the graph module 1112 can determine whether the blockchain includes an existing sidechain that is associated with the identifier. Upon determining that there is no existing sidechain for the identifier, the graph module 1112 can add the block onto the blockchain 1110 for distribution to the plurality of nodes 1102 and storage in the plurality of graph databases, in such a manner that the block initiates a sidechain off of the blockchain 1110. In sum, the computational architecture 1100 may support a blockchain 1110 that includes a plurality of sidechains, and each sidechain may be associated with a different identifier that is representative of a different asset. Sidechains can be created for each asset, so that action on the same asset can be recorded linearly on the corresponding sidechain. Therefore, blocks added onto the a given sidechain may all be related to the same asset.

Approaches to Graphically Modeling Distributed Information

Introduced here is an approach to combining two technologies—a graph database and blockchain—in such a way that implicit and explicit relationships between disparate data can be established. To accomplish this, a graph module can employ ML or AI algorithms to learn the relationships between data stored in various blocks of one or more blockchains. These relationships can then be represented in the form of graph models. At a high level, these graph models associate blocks that provide context to other blocks in the blockchain(s).

The computational architecture discussed above with reference to FIGS. 1 and 3-11 can be used to graphically model the relationships between data on one or more blockchains. The computational architecture represents a complex set of constructs, nodes, protocols, and functions that collectively create a data storage platform that is auditable and immutable.

A. Graph Databases

As mentioned above, the computational architecture uses nodes to store data. These nodes may use a world state (e.g., world state 808 of FIG. 8) to create, read, update, or delete data. The world state may allow blocks to be stored in a graph model, while also supporting querying capabilities that are analytics, direct, or graph based. Normally, the world state is deployed in conjunction with the nodes of the computational architecture. For the nodes, a graph database may be chosen as the storage medium since it allows for transactional and analytical queries in addition to graph queries. Graph databases also represent real-world information more natively to how it really is (and thus are well suited for ML and AI). The graph database may be designed, structured, or otherwise employed to support the creation of graphs as further discussed below.

B. Defining Edge Relationships

Graph databases require a digital record (i.e., a graph node) to have explicit relationships—referred to as "edges"—be defined before queries are performed. Implying or inferring these relationships at query time can be computationally expensive (and tends to be time consuming), so it is beneficial to define at least some of these relationships before query time. Using edges, data can be given context.

There are three main approaches to defining edge relationships. First, predefined edge relationships may be codified in a data structure (also called a "dictionary"). As an example, an edge relationship may be "predefined" is a patient "HAS_A" surgery if the asset corresponding to the surgery includes the MRN associated with the patient. Predefined edge relationships can be automatically created based on known relationships that are surfaced by codified rules. Second, edge relationships can be created after assets are recorded in the blockchain. These "post-persistence" edge relationships could be dynamically created based on outside influence (e.g., input from a user) and insights gained from other data, as opposite to the predefined edge relationships that are automatically created based on existing definitions in the dictionary. Third, edge relationships can be learned through automated analysis of graph models. A graph module (e.g., graph module 1112 of FIG. 11) may be responsible for managing the processes by which edge relationships are defined.

FIG. 12 includes a high-level illustration of a process by which an algorithm can be learned for predicting, inferring, or otherwise determining relationships between dissimilar data. The algorithm could be an ML algorithm or AI algorithm. As mentioned above, this process may be performed by a graph module (e.g., graph module 1112 of FIG. 11) that is responsible for training and then deploying the algorithm.

At a high level, this is the process by which the graph module can train the algorithm to learn relationships between data in a database 1202. As an example, the data in the database 1202 may relate to health-related entities such as patients, providers (e.g., healthcare systems, healthcare facilities, and healthcare professionals), payers (e.g., insurers), manufacturers of medical equipment, pharmaceutical companies, and the like. These data may be derived from a single source (e.g., a healthcare system), or these data may be derived from multiple sources (e.g., a healthcare system, insurers, and manufacturers of medical equipment).

The goal of the learning algorithm 1204 may be to learn relationships between data in the database 1202 in a consistent manner to ensure that relationships are accurately predicted post-deployment (e.g., in the graph module 1112 of FIG. 11). Consider, for example, a scenario in which the database 1202 includes (i) patient medical records and (ii) healthcare system records of medical equipment used during procedures. By analyzing this data, the learning algorithm 1204 may learn how to identify relevant procedures through analysis of the patient medical records and then "match" those relevant procedures with the medical equipment used.

Normally, the learning algorithm 1204 is an unsupervised ML algorithm, such as a neural network, that can be trained to learn relationships between data. For example, "raw" data could be provided, as input, to the learning algorithm 1204 in the form of training data, and the learning algorithm 1204 may predict relationships between pieces of the "raw" data as output. As another example, a series of graph models could be provided, as input, to the learning algorithm 1204 in the form of training data, and the learning algorithm 1204 may propose edge relationships as output. Therefore, the learning algorithm 1204 may be able to learn how to discover relationships through analysis of data in different forms, for example, based on the preferred form for inputs and/or outputs. Note that the edge relationships—regardless of how they are defined—may be associated with a particular blockchain (and thus the data stored thereon). These learned relationships 1206 can be used to surface insights into data to which the learning algorithm 1204 is subsequently applied.

After training has concluded, the learning algorithm 1204 may be deployed to the graph modules within a computational architecture. As mentioned above, each node in the computational architecture may include a graph module in some embodiments, while in other embodiments, only some nodes may include a graph module (and thus the learning algorithm 1204). As part of an inferencing stage, the graph module may acquire, receive, or otherwise obtain data 1210 to be analyzed. Thereafter, the graph module can apply the learning algorithm 1204 to the data 1210 and then produce, as output, one or more edge relationships 1208. Each edge relationship may be representative of a contextual relationship between data that can be embodied programmatically as an interconnection between the data.

Accordingly, edge relationships can be a priori, and as such can be predefined in a dictionary or learned through automated analysis. Definitions for edge relationships can be used by the computational architecture to create edges between graph nodes in the graph database at write time or read time. In some embodiments, some edge relationships (e.g., those corresponding to implicit or learned edges) may be created following the create time of the corresponding graph node. The computational architecture may create edges indicating the relationships between transactions, blocks, sidechains, or any combination thereof. When combined with predefined edges, these runtime edges can provide an extremely rich context for the blocks that has not traditionally been available.

C. Creating Graph Models

Referring again to FIG. 11, the computational architecture 1100 may manage a blockchain 1110 on which blocks (e.g., data blocks 302, consent blocks 402, or receipt blocks 502 of FIGS. 3, 4, and 5, respectively) are stored. In some embodiments, the computational architecture 1100 is designed to create sidechains for different assets. Thus, a separate sidechain may be created for each asset, as identified with a corresponding asset ID, such that each action involving the same asset can be recorded linearly on its corresponding sidechain. These sidechains may be directly accessible via corresponding APIs. Since the computational architecture 1100 is highly configurable, an administrator may be able to extend the definitions stored in the dictionary based on additional information. Assume, for example, that the administrator is interested in complementing the data stored on the computational architecture 1100 with human resources ("HR") data and employment data. The administrator may be able to easily accomplish this through APIs that permit the graph module 1112 to access the HR data and employment data. Upon accessing this data, the graph module 1112 may be able to learn relationships with the data stored on the computational architecture 1100 (e.g., via the use of ML or AI algorithms), or the administrator may be able to define relationships with the data stored on the computational architecture 1100 (e.g., via an interface accessible on a computing device). Accordingly, the administrator may be able to produce graph models quickly for various use cases.

The power of the graph module 1112 is not limited to graph models of a given space, but also extends to undiscovered connections in those graph models and the potential connections to other graph models in the network. APIs implemented by, or accessible to, the graph module 1112 may allow for various ML and AI algorithms to discover these relationships. For example, the graph module 1112 may apply an algorithm that uses graph theory in order to detect and then analyze relationships, for example, using the A* algorithm or Dijkstra's algorithm.

Figure 13:
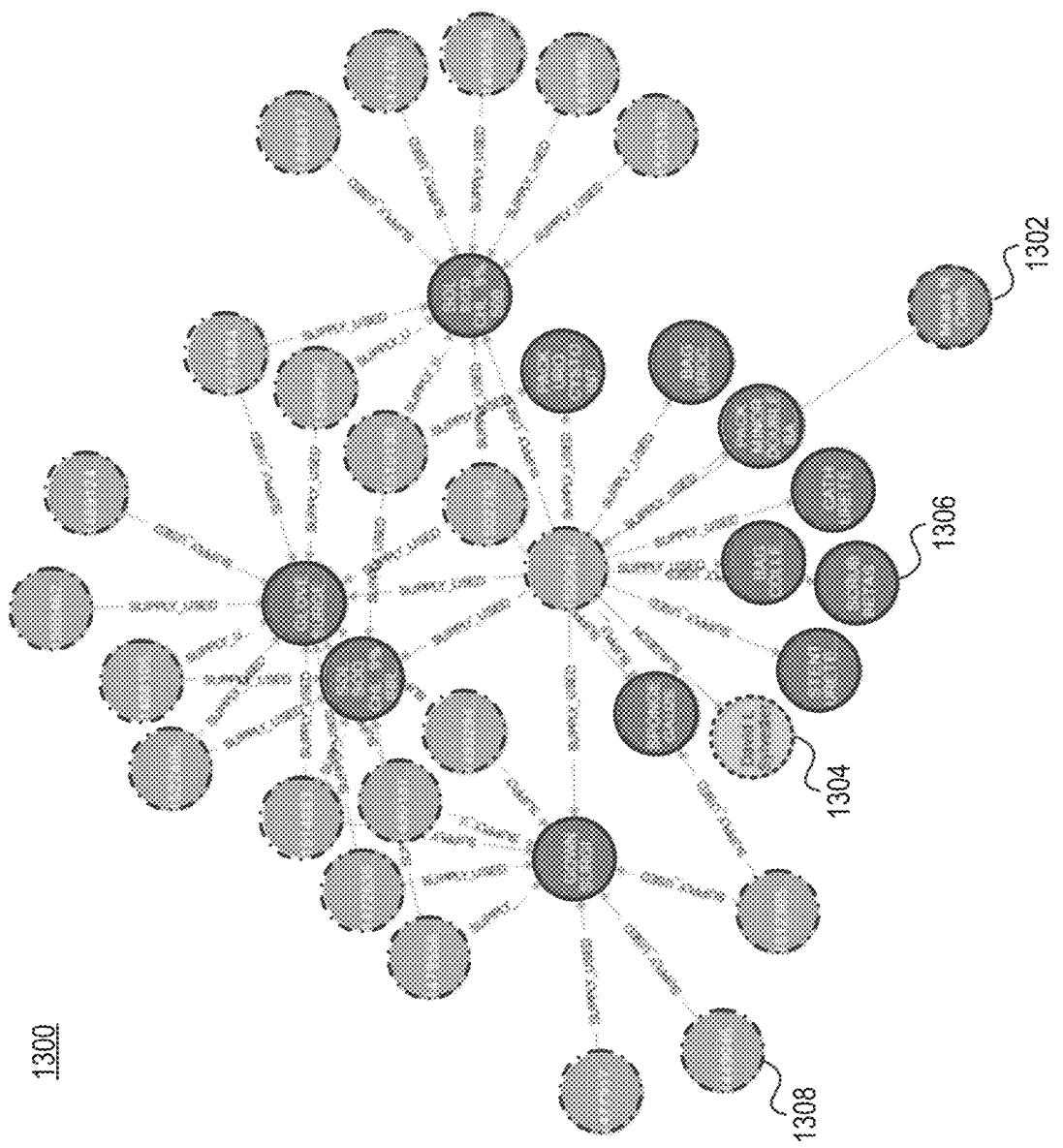
FIG. 13 includes an example of a graph model that considers data distributed across different blocks of a blockchain.

FIG. 13 includes an example of a graph model 1300 that considers data distributed across different blocks of a blockchain. In FIG. 13, the dash graph node 1302 corresponds to a patient and the dot graph node 1304 corresponds to a healthcare professional. Meanwhile, the solid graph nodes 1306 correspond to different healthcare products, while the half dash dot graph nodes 1308 correspond to different surgical procedures. Here, the patient, healthcare professional, and healthcare products are representing via text strings, and each surgical procedure is represented using a numeric string.

FIG. 13 illustrates how different types of graph nodes can be connected via different types of edge relationships. Here, for example, the dash graph node 1302 is connected to a half dash dot graph node to indicate that representative patient Maria N. Cobb was involved in a surgical procedure. Meanwhile, the half dash dot graph node is connected to the dot graph node 1304 to indicate that representative healthcare professional David L. Sylvester was involved in the surgical procedure, and the half dash dot graph node is also connected to a series of solid graph nodes to indicate which healthcare products were used in the surgical procedure. As an example, FIG. 13 indicates that a certain type of surgical gown was used during the surgical procedure. Through the interconnections between different graph models, it can be seen that the same type of surgical gown was used in eight other surgical procedures.

Those skilled in the art will recognize that the example shown in FIG. 13 is provided solely for the purpose of illustration. Graph models can be visualized in various ways, and the example shown in FIG. 13 is not intended to limit the present disclosure.

Methodologies for Implementing Computational Architecture

FIG. 14 includes a flow diagram of a process 1400 performed by a computational architecture for committing a block to a blockchain, for storage in a plurality of graph databases that are distributed amongst a plurality of nodes. Initially, a computational architecture can provide (i) a plurality of nodes that collectively implement a blockchain and (ii) a plurality of graph databases that are distributed amongst the plurality of nodes (step 1401). Each of the plurality of nodes can include a processor and associated memory that are executable by the processor to generate a hash value upon receiving input indicative of a request to store first data in the corresponding graph database (step 1402) and upon confirming that the hash value has also been generated by a majority of the plurality of nodes, create a first block that includes (i) the first data and (ii) the hash value (step 1403). The instructions may be further executable by the processor to determine that a contextual relationship exists between the first data in the first block and second data in a second block that is part of the blockchain (step 1404). As mentioned above, this could be accomplished using a dictionary or a trained algorithm.

Moreover, the processor may populate information regarding the contextual relationship in the first block (step 1405) and then add the first block onto the blockchain for distribution to the plurality of nodes and storage in the plurality of graph databases (step 1406). While contextual relationships (also called "edge relationships") may be part of the data that is stored in the first block, the contextual relationships may not always be known at the time of block creation. Accordingly, contextual relationships could be derived before, during, or after block creation.

In some embodiments, the instructions are further executable by the processor to model the contextual relationship by representing the first and second blocks as graph nodes in a graph data structure and interconnecting the graph nodes with an edge to indicate the relationship (step 1407). For clarity, these actions may be described as being performed in sequence; however, those skilled in the art will recognize that these actions are normally performed contemporaneously, such that the graph nodes are created and interconnected at the same time.

FIG. 15 includes a flow diagram of a process 1500 performed by a computational architecture for committing a dynamically configurable block to a blockchain, for storage in a plurality of graph databases that are distributed amongst a plurality of nodes. Initially, a computational architecture can provide (i) a plurality of nodes that collectively implement a blockchain and (ii) a plurality of graph databases that are distributed amongst the plurality of nodes (step 1501). Each of the plurality of nodes can include a processor and associated memory that are executable by the processor to generate a hash value upon receiving input indicative of a request to store first data in the corresponding graph database (step 1502) and upon confirming that the hash value has also been generated by a majority of the plurality of nodes, configure a first block to have an appropriate field count, an appropriate field size, and/or an appropriate field schema to accommodate the first data (step 1503) and populate the first data in the first block (step 1504). This allows the first block to be designed and sized in a tailored manner for the first data.

The instructions may be further executable by the processor to determine that a contextual relationship exists between the first data in the first block and second data in a second block that is part of the blockchain (step 1505). As mentioned above, this could be accomplished using a dictionary or a trained algorithm. In some embodiments, the second block is part of the "main chain" of the blockchain, while in other embodiments, the second block is part of a sidechain. As discussed above, the blockchain could include a plurality of sidechains, for example, relating to different assets. The processor can then populate information regarding the contextual relationship in the first block (step 1506) and then add the first block onto the blockchain for distribution to the plurality of nodes and storage in the plurality of graph databases (step 1507).

Because the field count, field size, and field schema are dynamically configurable, blocks may have different values for those parameters. Assume, for example, that the processor receives input indicative of another request to store third data in the corresponding graph database. In such a scenario, the processor can generate a second hash value and upon confirming that the second hash value has been generated by a majority of the plurality of nodes, configure a third block to have an appropriate field count, an appropriate field size, and/or an appropriate field schema to accommodate the third data, and populate the third data in the third block. Usually, the field count, field size, and field schema configured for the third block is different than the field count, field size, and field schema configured for the first block, to account for differences between the third data and first data.

Benefits of Graphically Modeling Distributed Information

Utilizing the computational architecture described above for storage of data has several notable benefits. First, configuration of data into smart data objects that are made immutable after being committed to the blockchain increases the security, integrity, and analytical capacity of that data. For example, not only is the data stored in the blocks on the blockchain immutable, but ownership is embedded into the same immutable smart data object, improving security and privacy of that data. Multiple layers of permissions can be set governing which entities have access to the data and how data is to be localized to subnetworks on the network. Accordingly, the computational architecture can be used to share data in a secure, controller manner that addresses the drawbacks of traditional data management solutions.

Second, the nature of the computational architecture allows business data, as may be stored on data block 302 of FIG. 3 and graph data block 1002 of FIG. 10, and transactional data, as may be stored on consent block 402 of FIG. 4A, smart contract block 434 of FIG. 4B, and receipt block 502 of FIG. 5, to be co-located on the same blockchain. This allows the user to seamlessly analyze both business data and transaction data through a single interface; eliminating the need to download, aggregate, and restructure the data prior to analysis.

Additionally, the computational architecture provides several levels of data contextualization, which significantly enhance analytical processes. The metadata and edge relationships afforded by the smart data object of the graph data block 1002 provide two sources of context. The position of a block in context to other blocks on the blockchain provides an additional context that may be useful in analysis. And lastly, the application of ML and AI to create implied relationships offers a third layer of context.

The configuration of data as smart data objects and the layers of context afforded by the computational architecture may also confer a higher degree of trust in the authenticity and integrity of the data asset (e.g., asset 306 of FIG. 3 or asset 1006 of FIG. 10). As an example, a recipient of a first data asset may view such data together with (a) its signature and hash, thus proving the first data asset has not been altered, (b) a second data asset that has an explicit relationship with the first data asset and represents a third-party verification of the first data asset, thus proving that a trusted authority has attested that the first data asset is accurate, or (c) the source information or history of the first data asset, thus proving its lineage.

As mentioned above, there are some situations where data stored on the computational architecture is most useful when considered in combination with, or in context to, other data stored on the computational architecture. Understanding and correlating the data in different blocks on the blockchain can be quite difficult. This is especially true if those blocks share more than one feature (also referred to as an "attribute") in common. It is also quite difficult to combine and correlate data that is owned by different owner IDs, subject to different consent contract(s), and/or located on different chains, without stripping the data of these ownership, access controls, and location requirements. Introduced here are approaches to learning and then graphically modeling the relationships between data stored on a computational architecture and producing visualizations of those relationships, while preserving ownership, access controls, and data location. Thus, the computational architecture may produce graph models to indicate the relationships between various data and then create visualizations of those graph models. These visualizations tend to take the form of diagrams in which attributes are represented by graphical elements that are interconnected via edge relationships. Note that these graphical elements may also be referred to as "nodes," so the term could be used to refer to graphical elements in visualizations or computing devices in a distributed network. For the purposes of clarity, "nodes" as used herein is generally used to refer to computing devices in a distributed network and "graph nodes" is generally used to refer to graphical elements in visualizations.

For the purpose of illustration, several scenarios in which these visualizations are helpful are provided below:

Onboarding and Credentialing: There is a lengthy process for credentialing healthcare professionals as those individuals leave one practice for another. Often, this process involves months of work by the new practice (or credentialing service) to verify all of the credentials of the new employee. For example, the new practice may not only need to confirm previous employers, but also verify degrees from universities, certifications from boards, and other honorariums. This process occurs anew whenever a healthcare professional moves to a new practice, leading to significant losses in terms of cost and time. Imagine, however, a scenario where this information is stored and validated on a blockchain. Relationships between healthcare professionals and their past and present employers, educational institutions, continuing education providers, verifiers, accrediting bodies, and other healthcare providers could be readily surfaced through the graph models afforded by the computational architecture introduced herein. For example, the computational architecture may be able to easily identify healthcare professionals who share an attribute in common (e.g., graduated from the same university, have the same board certification) by determining which graph models are interconnected via the corresponding graph node. In another example, the computational architecture may be able to identify the relationship between a healthcare professional, the university from which she graduated, and the independent verifier that verified the provider's degree title and graduation date. This information, configured as smart data objects, allows a new employer to quickly (or even in an automated fashion) assess what verifications have been completed and when, so onboarding and credentialing processes can be focused only on those verifications that are expired or missing, rather than re-verifying all information. The financial implications of this expediency cannot be overstated. Given that turn-over for nurse professionals can exceed 50 percent per year in many cases, healthcare employers may save millions or even billions of dollars by streamlining the onboarding and credentialing process.

Recruiting: As further discussed below, a graph model can have trust and context built into it. In the case of a healthcare professional, the graph model can include graph nodes corresponding to verified skills, trainings, continuing education (CE) credits, and other verified achievements, in addition to formal degrees and certificates. In a sense, a graph model can be used as a definitive and trusted profile for a person, and these graph models may serve as the basis for ML or AI algorithms to match job listings with qualified candidates. These algorithms can be made more efficient and accurate with access to information regarding informal skills in addition to formal training. Moreover, these algorithms may be trained to account for others' graph models as well. For example, rather than determine the suitability of a given person "in a vacuum," these algorithms could instead determine the suitability of the given person in the context of other candidates or other employees who have succeeded or struggled in similar positions with similar skill sets. Moreover, in determining the best candidate for a given job posting, an algorithm can examine other graph models to better understand the skills of other individuals when those individuals entered comparable positions, how those individuals subsequently performed in those comparable positions, and how certain attributes might predict performance of a given candidate in the role required by the given job posting.

Engagement and Retention: After a healthcare professional has been onboarded, an algorithm could be applied to her graph model to optimize engagement and professional development. As an example, an algorithm can be applied that identifies and visualizes the relationships between the company's skill gaps, the employee's attributes, and the attributes of other professionals who have acquired the gap skills. This can be used to identify employees who are most likely to succeed in skill gap areas and present such employees with personalized professional development opportunities that align the employee's personal success with the company's corporate success. Similarly, an algorithm could be applied to the graph models associated with some or all of the employees in an effort to determine what attributes are helpful in retaining talent. Understanding how the career path of a healthcare professional fits corporate needs may allow the employer to guide the healthcare professional to better growth opportunities (e.g., formal and informal skills development) that lead to long-term success.

Care Quality: As health systems move into value-based reimbursement models, in which the provider is financially incentivized to practice preventative medicine and keep patients healthy, it is critical for the health system to be able to understand whether or not a provider's interventions are having the intended preventative effect. In this scenario, the treatments and interventions prescribed by a given healthcare professional may be visually illustrated via a graph model, illustrating the primary and secondary relationships between healthcare professionals, their interventions, the downstream health outcomes experienced by their patients, and even the correlations between patient attributes and intervention attributes. For example, the computational architecture may be able to easily identify interventions that are effective for patients with certain attributes, or healthcare professionals whose quality is above average for patients with certain attributes, by determining which graph models are interconnected via the corresponding graph node. In this way, healthcare professionals can easily develop personalized care plans for patients that are more likely to result in adherence and successful patient outcomes, because they are informed by the patient's unique context and the correlated outcomes from similarly situated patients.

Consent: Whenever a patient wishes to visit a new healthcare professional or healthcare facility, she may need to obtain her own medical records or provide consent to grant access to those medical records. This process can be lengthy, difficult, and confusing. Usually, the patient must present herself in person, sign release forms, and then transport the medical records to the next appointment. However, consider a scenario where the medical records are directly owned and controlled by the patient rather than another entity (e.g., a healthcare facility or record-keeping service). Various medical records can be programmatically combined across different electronic medical records ("EMRs") to create a graph model that represents a unified view of the medical history of the patient. The data within the graph model can be directly consented by the patient using the consent mechanisms described above. The patient may not only be able to consent to access by a new entity, but the patient may also be able to revoke access by an existing entity.

Informed and Dynamic Consent for Clinical Research: When patients enroll in clinical research studies, the study sponsor is required to get informed consent from each patient prior to enrollment. Ensuring that patients truly understand the nature of the study can be challenging. Using the computational architecture herein, a patient can be presented with a personalized informed consent process that presents the relevant information in a coherent manner and delivery modality that is most accessible and understandable by each patient. In addition, the certifications of understanding and e-signatures provided by the patient at the conclusion of the informed consent process are stored immutably and in context to the study information that was presented to the patient. The study sponsor can confidently present this data to compliance officers and regulatory authorities. Once enrolled, sponsors are required to provide mechanisms for patients to change or revoke their consent after the initial informed consent process (this is called "dynamic consent"). Because traditional data management systems effect data exchange using direct data transfers, honoring a patient request to revoke their consent can be logistically challenging, if not impossible. Using the computational architecture herein, however, the sponsor can easily provide patients with the ability to easily revoke consent, with such revocations taking immediate effect.

Information Exchange: Health information exchanges ("HIEs") are designed to make the medical record of a person available to all providers in a region (e.g., a state) so that, if the person is unable to provide consent to her data (e.g., due to an emergency), the data can be retrieved without consent and the person can receive appropriate care. However, HIEs suffer from several problems. First, HIEs tend to offer poor traceability with regard to how data is accessed and shared, which means that there is often poor visibility into which entities are using the data (and how those entities are using the data). Second, HIEs are normally set up as either a data warehouse (i.e., with persistent data storage) or middleware that manages connections between different entities (i.e., without persistent data storage). Role-based access tends to be used regardless of the form, and this makes managing access prohibitively challenging. Third, while HIEs are normally able to handle clinical data without issue, the underlying infrastructure is not well suited to handle more diverse types of data, such as Internet of Things ("IoT") data and behavioral health data. The computational architecture described above is able to address these problems. In fact, surfacing interconnections between various attributes through graph models may allow new services to be provided that were not previously possible, such as deep analytics that make recommendations regarding personalized medicine. In addition, this computational architecture described above makes it possible to analyze populations across a multitude of health systems while maintaining the ownership, access controls, and location requirements of the underlying data.

Supply Chain: Tracking the state of a specimen from collection, transport, receipt, analysis, and delivery can be burdensome. All of these steps are critical in ensuring that the specimen is properly handled. To ensure that this is done properly, various properties (e.g., temperature, humidity, weight, etc.) can be tracked at each step. Increasingly, supply chains involve multiple parties (e.g., organizations and patients) that each desire to share data selectively with the other parties. Using the computational architecture described above, timestamps and data for these steps can also be recorded to the blockchain, and each party is able to selectively share data with other parties at the appropriate time and under the appropriate conditions. A graph model could be created that catalogues these steps, and thus allows issues (e.g., delays) and potential efficiencies to be detected more easily.

Engagement: As health care moves toward preventative and personalized medicine, healthcare professionals and payers (e.g., insurers) have continued to look for ways to engage with patients to drive those individuals toward healthier lifestyles. Traditional data management solutions are not equipped to bring together diverse types of data (and are even less suitable when consent and governance of that data is considered). Graph models can be used to provide a more comprehensive view of a patient, including not just health information but also behavioral data, social data, movement data, location data, and the like. For example, the graph model created for a given patient may indicate relationships to other patients, healthcare professionals, and healthcare products. Moreover, the graph model may provide context by specifying, for example, the location of her primary care provider, from which information into weather, allergens, and the like could be determined. The relationships discovered through analysis of the graph models allow for deeper insights into engagement since the computational architecture can determine, based on analysis of thousands or millions of other patients, what has worked for patients who are similar to the one of interest.

Orchestration and Automation: Automation algorithms can be trained to look for certain data conditions and then take a specific action based on those conditions. For example, an automation algorithm may be trained to identify whether a verification is linked to the degree of a healthcare professional and, if so, determine the date that the verification was added to the blockchain. If the verification is less than a predetermined age (e.g., 3 years), the automation algorithm may initiate a verification procedure and then inform the credentialing administrator that verification has already been completed. As another example, if a patient is undergoing cell gene ("CG") treatment, an automation algorithm may monitor specimens as collected from the patient and transported to a healthcare facility for manufacturing of the CG treatment. After data enters the blockchain indicating that manufacturing of the CG treatment is complete, the automation algorithm may execute a process to schedule the patient for infusion. In both examples, the automation algorithms may rely on validated and connected data that includes context and has been deemed trustworthy, and shares that data only when certain conditions have been met.

Identity Management: Identity management is becoming a more pressing issue as it raises questions regarding how sensitive data is managed. Traditional data management solutions tend to rely on centralized registries (e.g., that are controlled by government agencies), but these registries are prone to unauthorized access. Moreover, there is very limited control over the sensitive data stored in these registries, so the sensitive data can be shared or edited without consent from the owners. As mentioned above, the computational architecture described herein allows individuals to take direct control of their data. For example, after identity data associated with a given person has been validated by a trusted third party (e.g., an identity verification service), the identity data can be added to the blockchain, as well as the third-party verification, and then populated into the graph model created for the given person. Population into the graph model adds further trust to the identity data since relationships to other data associated with the given person are made clear.

Collaborative Research: When researchers from different organizations want to collaborate with each other, data about the research must be shared. However, these researchers may want to share the data without losing control over it. In addition, researchers may want to study the relationship of their research findings to the findings of other collaborating researchers, thus uncovering new discoveries that would not otherwise be discoverable. Both can be accomplished using the computational architecture described herein. Moreover, information such as test results, test subjects, and the like can be interrelated through a graph model.

Marketplaces: Consider, for example, how many different entities may require access to data to personalize services provided to a patient. These entities may include healthcare professionals, healthcare facilities, manufacturers of healthcare products, payers (e.g., insurers), and the like. Rather than share all of the data with each entity, the patient could instead control the data to which each entity is granted access. These permissions could also be made clear through the graph model created for the patient. For example, the patient may be able to specify which portion(s) of her graph model are to be accessible to each entity. Such an approach allows for services to be provided in a personalized manner without unlimited—in terms of scope or time—access of the data.

Accordingly, the computational architecture could build graph models for individuals (e.g., patients and healthcare professionals), specimens, healthcare products (e.g., pharmaceuticals, vaccines, medical equipment), buildings (e.g., clinics), rooms (e.g., operating rooms), organizations (e.g., providers and payers), and the like. Nearly anything could serve as the basis for a graph model, so long as its attributes can be programmatically associated with one another. The computational architecture can then use ML or AI algorithms to better understand the relationships between various graph models. The benefit of this approach is that the computational architecture can surface relationships that might otherwise be difficult to determine. As an example, in the context of a recall of a healthcare product, the computational architecture may enable end-to-end traceability in a manner that traditional data management solutions cannot accomplish, so the impacted healthcare products (and thus affected patients) can be easily identified.

Another notable benefit of the computational architecture is that modeling "proven" data into graph models allows ML and AI algorithms to gain deeper insights. For example, an algorithm may be able to query across owned and consented data through a single application programming interface (API), even though the data itself may be housed across different nodes or networks, without needing to aggregate and reformat the data. The data that is queried may contain both the data itself and all of the underlying context (e.g., ownership, history, source, verification, relationships). This means that the algorithm (i) can operate more efficiently by running a single query across tens, hundreds, or thousands of nodes or networks, (ii) can operate on real-time data rather than static (and potentially outdated) data, and (iii) can gain additional context that makes the analyses more meaningful.

Overview of Cloaking

Figure 16:
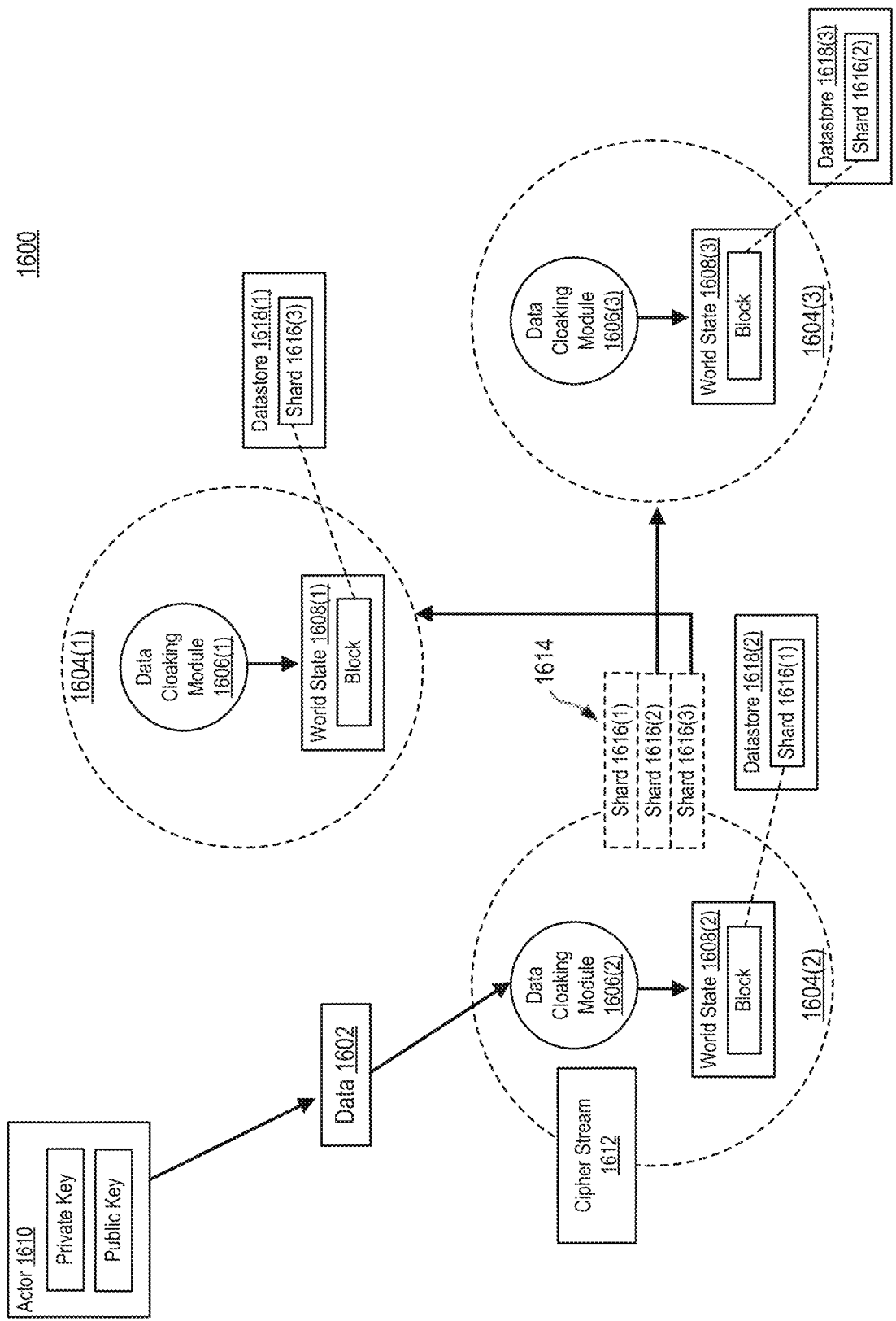
FIG. 16 illustrates how a data cloaking module (e.g., data cloaking module 1106 of FIG. 11) can implement data cloaking.
Figure 17:
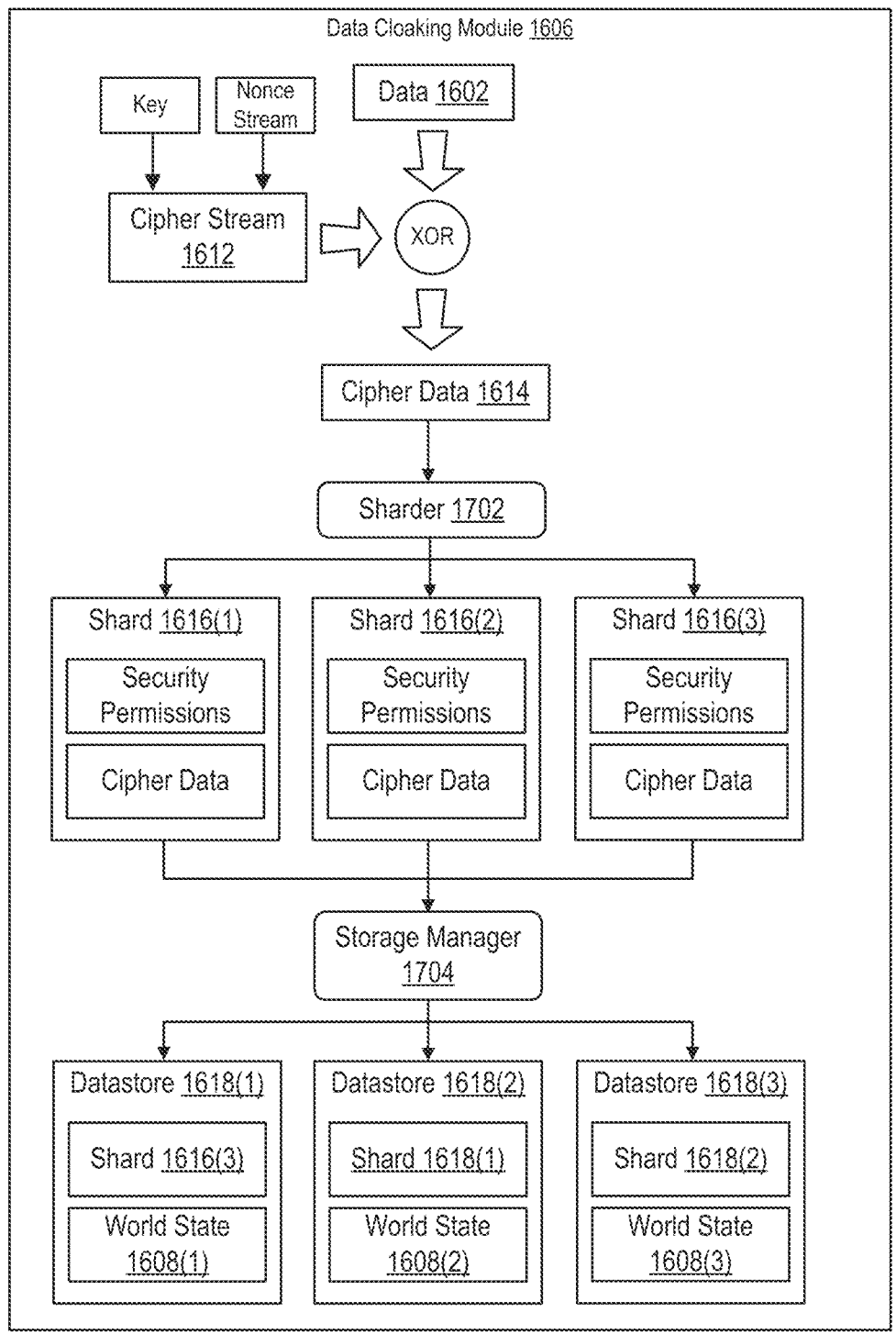
FIG. 17 is a schematic illustrating storage of data by the data cloaking module of FIG. 16.

FIG. 16 illustrates how a data cloaking module (e.g., data cloaking module 1106 of FIG. 11) can implement data cloaking. FIG. 17 is a schematic illustrating storage of data by the data cloaking module. FIGS. 16-17 are best understood when viewed together with the following disclosure.

After a consensus of trust has been established for an actor 1610, the actor 1610 can send data 1602 to a node 1604(2) of the computational architecture 1600. The data cloaking module 1606(2) within the node 1604(2) can create a cipher stream 1612 before or after receiving the data 1602. The cipher stream 1612 can be generated from a nonce stream and a public key associated with the actor 1610, for example. As the data 1602 is received—and prior to storing or transmitting within the computational architecture 1600—the data cloaking module 1606(2) can cipher the data 1602 using the cipher stream 1612 to generate cipher data 1614. For example, the data cloaking module 1606(2) may exclusive-OR ("XOR") the incoming data 1602 with the cipher stream 1612 to form the cipher data 1614. The cipher stream 1612 can be used similarly to decipher the cipher data 1614. This approach allows the computational architecture 1600 to handle large amounts of data without the need for the time and computational resources normally required for cryptographic functions. This approach may be referred to as "vertical data cloaking." The data cloaking module 1606(2) may implement vertical cloaking using the world state 1608(2) and one or more keys. As mentioned above, the world state 1608(2) may be representative of an immutable record of information committed to a blockchain. Keys used for cloaking the data 1602 may be a composite of a hash of previous, current, and subsequent blocks of data in the original clear text stream. These keys may be stored in a data rights management layer of the computational architecture 1600.

The data cloaking module 1606(2) can also implement "horizontal data cloaking" that subdivides the cipher data 1614 into a plurality of subsets that are then shared across multiple nodes 1604(1), 1604(3). These subsets may also be referred to as "sharded chunks," "shards," or "chunks" of the data 1602. As shown in FIG. 17, the data cloaking module 1606(2) can include a sharder 1702 that divides the cipher data 1614 into a plurality of shards 1616. In some embodiments, the shards 1616 are of equal size, and the final shard 1616(3) may be null-filled (e.g., padded with zeros) when not entirely filled with cipher data 1614. The data cloaking module 1606(2) can use multi-key management to protect each shard 1616 against information loss and to maintain strict access control to each shard 1616. Only permitted parties (e.g., the actor 1610 and any grantees) may be allowed to access the shards 1616. The shards 1616 that form a complete dataset (e.g., the cipher data 1614, and therefore the data 1602) may be referred to as an "information set."

Sharding can be performed independent of where the shards 1616 are ultimately stored. The shards 1616 may be stored within local datastores 1608 that are representative of graph databases as discussed above. Alternatively, the local datastores 1608 may be representative of another database management system, such as a relational database management system ("RDBMS") or non-tabular database (also called "NoSQL databases"). Additionally or alternatively, the shards 1616 could be stored in a global content addressable key space, for example, as implemented in a distributed hash table ("DHT") or directly in a blockchain.

For each shard 1616 created from the data 1602, a storage manager 1704 of the data cloaking module 1606(2) can determine at least one datastore 1608 for storing the shard and send that shard to the corresponding node 1604, while keeping the shards that are to be stored locally. For each shard 1616, the data cloaking module 1606—and more specifically, either the local module 1706 or receiving module 1708—can add a block defining the shard and its storage location to the world state 1608. Each block may also identify the source (e.g., the actor 1610) and structure (e.g., type of data) of the portion of the data 1602 within the corresponding shard 1616. As shown in FIG. 16, the data cloaking module 1606(2) stores a shard 1616(1) in its local datastore 1618(2) and creates the block within its world state 1608(2); the data cloaking module 1606(1) receives the shard 1616(3) from the node 1604(2), stores the shard 1616(3) in its local datastore 1618(1), and creates the block within its world state 1608(1); and the data cloaking module 1606(3) receives the shard 1616(2) from the node 1604(2), stores the shard 1616(2) in its local datastore 1618(3), and creates the block within its world state 1608(3).

As discussed above, the blocks written to the world state 1608 in one node can be automatically distributed to all of the other nodes 1604. Thus, the world state 1608 can contain immutable information as to the location of each shard 1616. The block within the world state 1608 defines the source and structure of data within its corresponding shard 1616, together with the location of the shard 1616 within the computational architecture 1600.

Periodically, within each node 1604, the storage manager 1704 can randomly select and send one or more locally stored shards 1616 to one or more other nodes 1604 for storage, and where the world state 1608 indicates that sufficient copies of each moved shard 1616 are stored within the computational architecture 1600, delete the local copy of that shard 1616.

Figure 18:
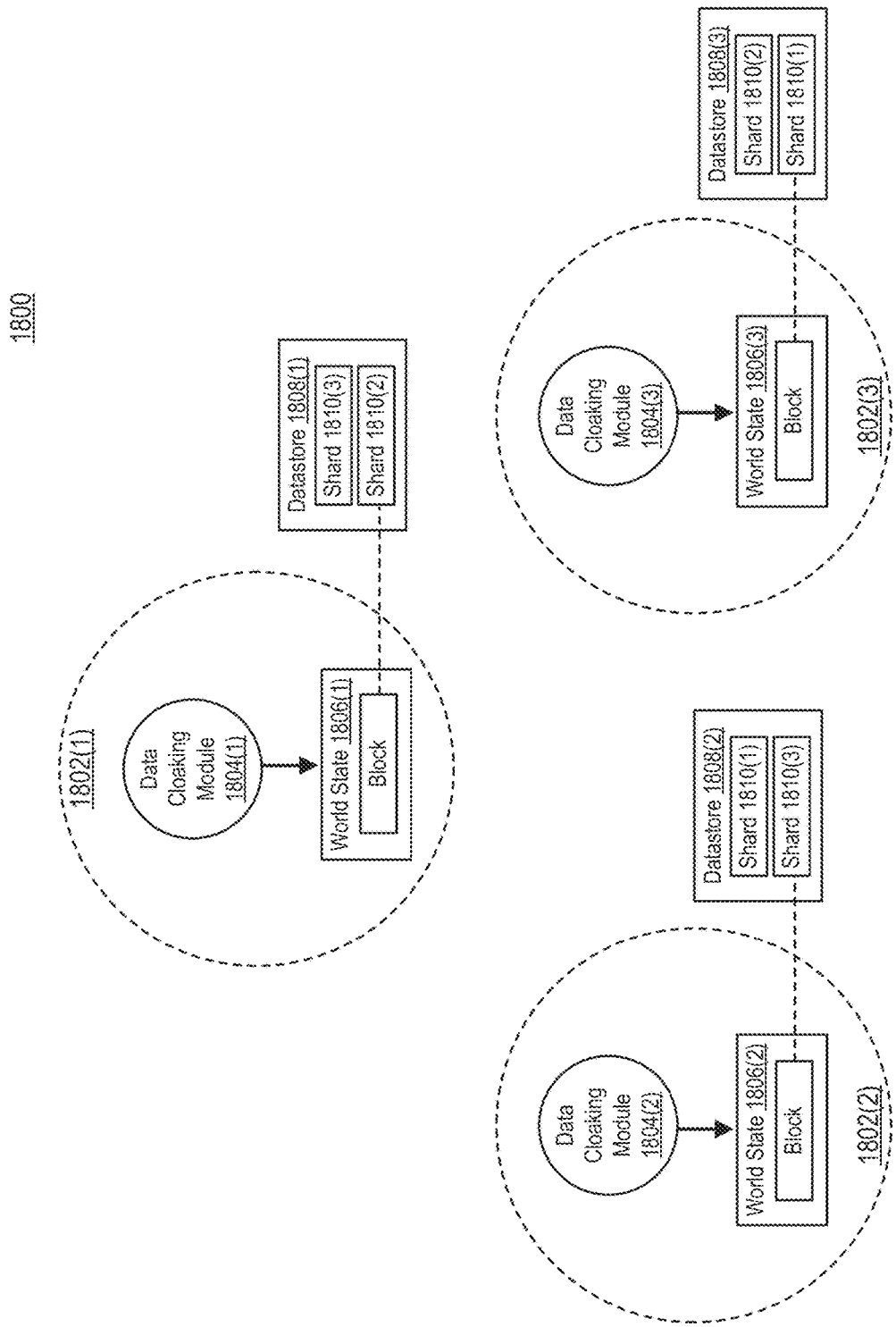
FIG. 18 illustrates a first maintenance step for distributing shards within a computational architecture.

FIG. 18 illustrates a first maintenance step for distributing shards 1810 within a computational architecture 1800. The computational architecture 1800 may be comparable to the computational architecture 1600 of FIG. 16. First, the data cloaking module 1804(1) sends a copy of the shard 1810(3) to the node 1802(2), the data cloaking module 1804(2) sends a copy of the shard 1810(1) to the node 1802(3), and the data cloaking module 1804(3) sends a copy of the shard 1810(2) to the node 1802(1). Second, the data cloaking module 1804(1) generates and stores, within its world state 1806(1), a block corresponding to the shard 1810(2). Third, the data cloaking module 1804(2) generates and stores, within its world state 1806(2), a block corresponding to the shard 1810(3). Fourth, the data cloaking module 1804(3) generates and stores, within its world state 1806(3), a block corresponding to the shard 1810(1). Thus, after the first maintenance step, the shards 1810 are further protected through redundancy.

Figure 19:
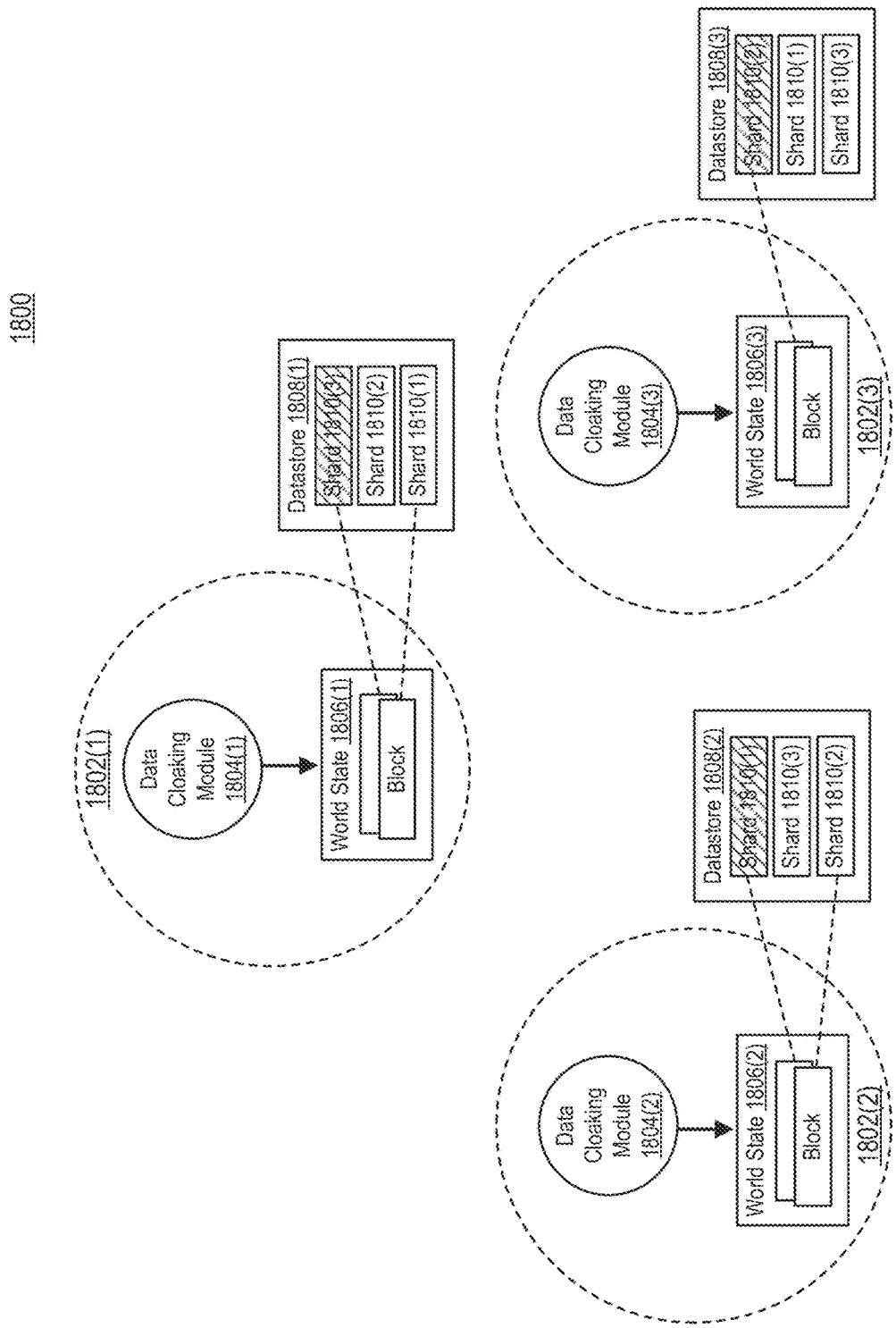
FIG. 19 illustrates a second maintenance step for moving the shards within the computational architecture.

FIG. 19 illustrates a second maintenance step for moving the shards 1810 within the computational architecture 1800. First, the data cloaking module 1804(1) sends a copy of the shard 1810(3) to the node 1802(3). The data cloaking module 1804(3) generates and stores, within its world state 1806(3), a block corresponding to the shard 1810(3) stored in the datastore 1808(3). The data cloaking module 1804(1) then deletes the shard 1810(3) from the datastore 1808(1), and generates and stores, within its world state 1806(1), a block corresponding to the deleted shard 1810(3).

Second, the data cloaking module 1804(2) sends a copy of the shard 1810(1) to the node 1802(1). The data cloaking module 1804(1) generates and stores, within its world state 1806(1), a block corresponding to the shard 1810(1) stored in the datastore 1808(1). The data cloaking module 1804(2) deletes the shard 1810(1) from the datastore 1808(2), and generates and stores, within its world state 1806(2), a block corresponding to the deleted shard 1810(1).

Third, the data cloaking module 1804(3) sends a copy of the shard 1810(2) to the node 1802(2). The data cloaking module 1804(2) generates and stores, within its world state 1806(2), a block corresponding to the shard 1810(2) stored in the datastore 1808(2). The data cloaking module 1804(3) deletes the shard 1810(2) from the datastore 1808(3), and generates and stores, within its world state 1806(3), a block corresponding to the deleted shard 1810(2).

Thus, the shards 1810 can periodically move location within the computational architecture 1800. Since the shards 1810 are not static and are distributed across more than one datastore 1808, the "attack profile" for hackers of the stored data is significantly reduced since the data is not in a single location and is constantly moving. This approach also provides "built-in" disaster recovery since the shards 1810 are stored in multiple locations, as shown in FIG. 19, such that catastrophic failure of any one location does not result in data loss. The computational architecture 1800 may include a different number of nodes 1802 without departing from the present disclosure.

Figure 20:
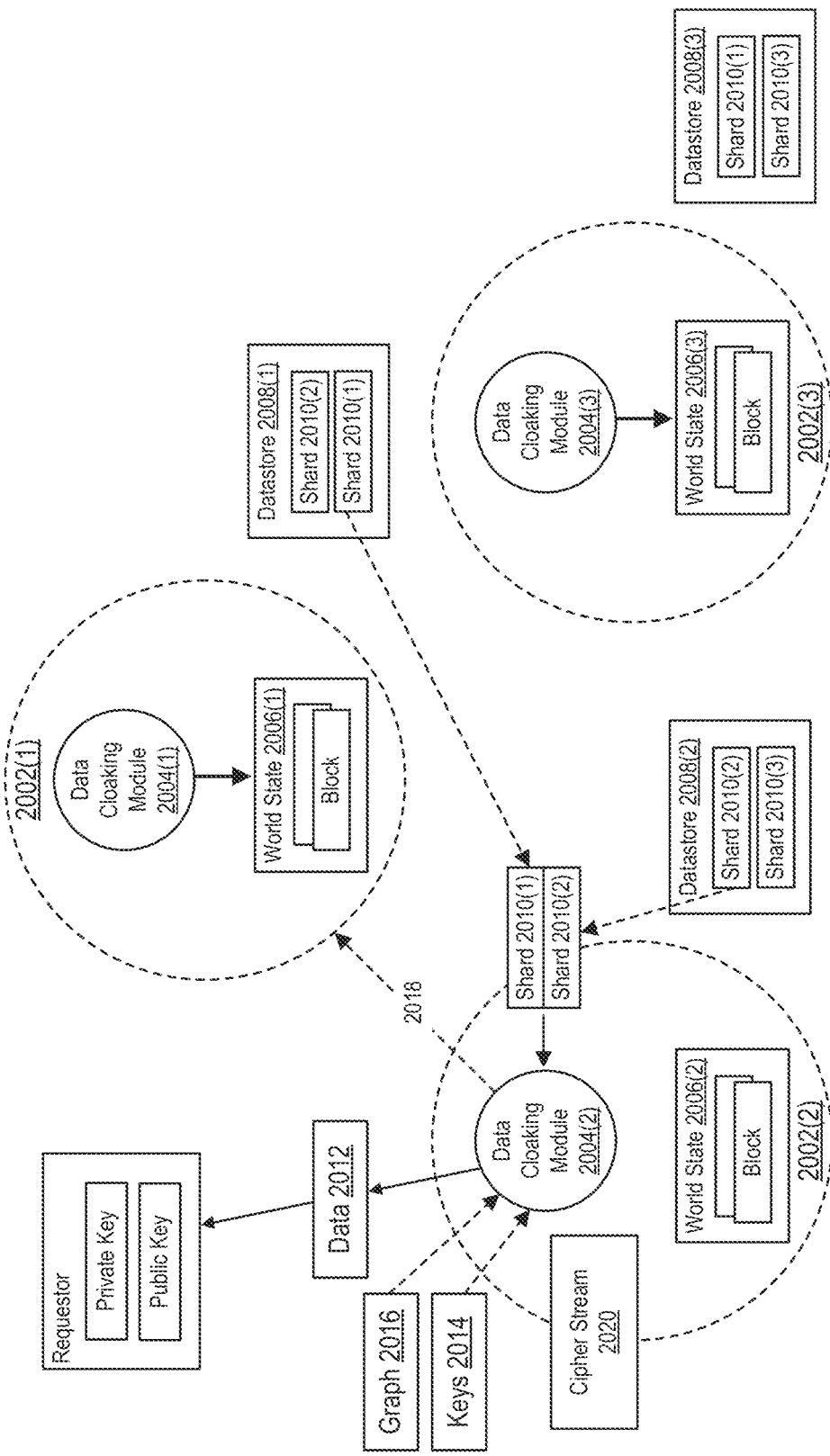
FIG. 20 illustrates how a data cloaking module can retrieve data.

FIG. 20 illustrates how a data cloaking module 2004 can retrieve data. To access any part or all of an information set (e.g., data stored in the asset 1006 of the graph data block 1002 of FIG. 10), the data cloaking module 2004 can search the world state 2006 for blocks corresponding to the shards 2010 of the data 2012. The data cloaking module 2004 can determine a topology of keys 2014 used to protect the shards 2010 and then compare that topology to a graph 2016 that represents the identity of the requestor. The data cloaking module 2004 then determines a current location (i.e., one or more nodes 2002 or datastores 2008) of each shard 2010 needed for the requested data, and then sends a message 2018 to each corresponding node 2002 requesting those shards from the determined locations. Where the data is stored local to the data cloaking module 2004, it can be retrieved directly from the corresponding datastore 2008. For example, based on the blocks, the data cloaking module 2004(2) sends the message 2018 to the node 2002(1) requesting the shard 2010(1) from the datastore 2008(1), and similarly retrieves the shard 2010(2) from the datastore 2008(2). Once the necessary shards 2010 are received, the data cloaking module 2004 can use the appropriate portion of the cipher stream 2020 to decipher the shards 2010 and form the data 2012.

Overview of Processing System

Figure 21:
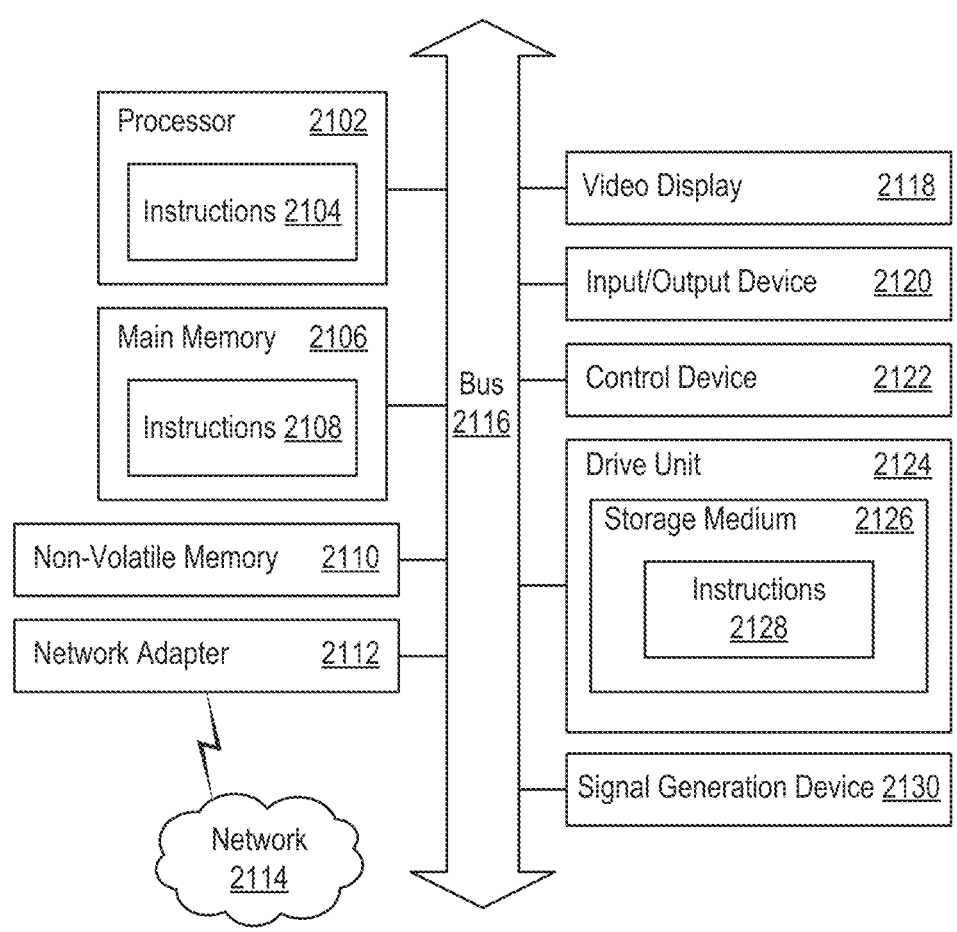
FIG. 21 includes a block diagram illustrating an example of a processing system in which at least some operations described herein can be implemented.

FIG. 21 includes a block diagram illustrating an example of a processing system 2100 in which at least some operations described herein can be implemented. For example, components of the processing system 2100 may be hosted on a computing device through which an individual is able to access the computational architecture introduced herein. As another example, components of the processing system 2100 may be hosted on a computing device on which aspects of the computational architecture are implemented.

The processing system 2100 may include a processor 2102, main memory 2106, non-volatile memory 2110, network adapter 2112, video display 2118, input/output devices 2120, control device 2122 (e.g., a keyboard or pointing device), drive unit 2124 including a storage medium 2126, and signal generation device 2130 that are communicatively connected to a bus 2116. The bus 2116 is illustrated as an abstraction that represents one or more physical buses or point-to-point connections that are connected by appropriate bridges, adapters, or controllers. The bus 2116, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), inter-integrated circuit (I²C) bus, or an Institute of Electrical and Electronics Engineers (IEEE) standard 1394 bus (also referred to as "Firewire").

While the main memory 2106, non-volatile memory 2110, and storage medium 2126 are shown to be a single medium, the terms "machine-readable medium" and "storage medium" should be taken to include a single medium or multiple media (e.g., a centralized/distributed database and/or associated caches and servers) that store one or more sets of instructions 2128. The terms "machine-readable medium" and "storage medium" shall also be taken to include any medium that is capable of storing, encoding, or carrying a set of instructions for execution by the processing system 2100.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 2104, 2108, 2128) set at various times in various memory and storage devices in a computing device. When read and executed by the processors 2102, the instruction(s) cause the processing system 2100 to perform operations to execute elements involving the various aspects of the present disclosure.

Further examples of machine- and computer-readable media include recordable-type media, such as volatile and non-volatile memory devices 2110, removable disks, hard disk drives, and optical disks (e.g., Compact Disk Read-Only Memory ("CD-ROMS") and Digital Versatile Disks ("DVDs")), and transmission-type media, such as digital and analog communication links.

The network adapter 2112 enables the processing system 2100 to mediate data in a network 2114 with an entity that is external to the processing system 2100 through any communication protocol supported by the processing system 2100 and the external entity. The network adapter 2112 can include a network adaptor card, a wireless network interface card, a router, an access point, a wireless router, a switch, a multilayer switch, a protocol converter, a gateway, a bridge, bridge router, a hub, a digital media receiver, a repeater, or any combination thereof.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A data storage platform comprising:
   a plurality of nodes that collectively implement a blockchain; and
   a plurality of graph databases that are distributed amongst the plurality of nodes,
      wherein each of the plurality of graph databases includes a persistent store of data committed to the blockchain, and
      wherein each of the plurality of graph databases is associated with a corresponding one of the plurality of nodes;
   wherein each of the plurality of nodes includes a processor and associated memory with instructions stored therein that, when executed by the processor, implement:
      a consensus trust module operable to:
         upon receiving input indicative of a request from an individual to store data in the corresponding graph database,
         generate a hash value that is representative of integrity of the data,
         distribute the data, updated with the hash value, to the other nodes of the plurality of nodes, and
         upon confirming that the hash value has also been generated by a majority of the plurality of nodes, create a block that includes the data; and
      a graph module operable to:
         apply a trained algorithm to the blockchain to autonomously learn a relationship between the data in the block and other data in another block that is part of the blockchain,
         populate information regarding the relationship in the block, so as to record the relationship with the another block, and
         add the block onto the blockchain for distribution to the plurality of nodes and storage in the plurality of graph databases.

2. The data storage platform of claim 1, wherein the graph module is further operable to:
   model the relationship by representing the block and the another block as graph nodes in a graph data structure and then interconnecting the graph nodes with an edge to indicate the relationship.

3. The data storage platform of claim 2, wherein the graph module is further operable to:
visually represent the graph data structure.

4. The data storage platform of claim 2, wherein the plurality of nodes is representative of a subset of all nodes that collectively implement the blockchain.

5. The data storage platform of claim 1, wherein the graph module is further operable to:
upon receiving input indicative of a query, employ another algorithm to search the corresponding graph database to determine whether a matching block that satisfies the query exists.

6. The data storage platform of claim 5, wherein the another algorithm is a depth-first algorithm.

7. The data storage platform of claim 5, wherein the another algorithm is a breadth-first algorithm.

8. The data storage platform of claim 1, wherein the block and the another block pertain to a same topic and include a same type of data.

9. The data storage platform of claim 1, wherein the request is submitted by the individual via a computing device that is representative of one of the plurality of nodes.

10. The data storage platform of claim 1, wherein each node of the plurality of nodes is representative of a separate computing device that includes the processor, the associated memory, and an interface for communication.

11. A data storage platform comprising:
a plurality of nodes that collectively implement a blockchain; and
a plurality of graph databases that are distributed amongst the plurality of nodes,
wherein each of the plurality of graph databases includes a persistent store of data committed to the blockchain, and
wherein each of the plurality of graph databases is associated with a corresponding one of the plurality of nodes;
wherein each of the plurality of nodes includes a memory with instructions stored therein that, when executed by a processor, cause the processor to perform operations comprising:
upon receiving input indicative of a request from an individual to store data in the corresponding graph database,
generate a hash value that is representative of integrity of the data, and
distribute the data, updated with the hash value, to the other nodes of the plurality of nodes,
upon confirming that the hash value has also been generated by a majority of the plurality of nodes, create a block that includes the data,
apply a trained algorithm to the blockchain to autonomously learn a relationship between the data in the block and other data in another block that is part of the blockchain,
populate information regarding the relationship in the block, so as to record the relationship with the another block, and
add the block onto the blockchain for distribution to the plurality of nodes and storage in the plurality of graph databases.

* * * * *